US012672969B2

(12) United States Patent (10) Patent No.: US 12,672,969 B2
Ruvalcaba et al. (45) Date of Patent: *Jul. 7, 2026

(54) OCCLUSIVE DEVICE

(71) Applicant: Covidien LP, Mansfield, MA (US)

(72) Inventors: Teresa Ruvalcaba, Newark, CA (US);
Earl Bardsley, San Clemente, CA
(US); Richard Rhee, Anaheim Hills,
CA (US)

(73) Assignee: Covidien LP, Mansfield, MA (US)

( * ) Notice: Subject to any disclaimer, the term of this
patent is extended or adjusted under 35
U.S.C. 154(b) by 72 days.

This patent is subject to a terminal dis-
claimer.

(21) Appl. No.: 18/926,071

(22) Filed: Oct. 24, 2024

(65) Prior Publication Data

US 2025/0049592 A1 Feb. 13, 2025

Related U.S. Application Data

(63) Continuation of application No. 17/807,025, filed on
Jun. 15, 2022, now Pat. No. 12,150,871, which is a
(Continued)

(51) Int. Cl.
*A61F 2/82* (2013.01)
*A61B 17/12* (2006.01)
(Continued)

(52) U.S. Cl.
CPC .......... *A61F 2/82* (2013.01); *A61B 17/12113*
(2013.01); *A61B 17/12163* (2013.01); *A61B
17/12172* (2013.01); *A61B 17/12177*
(2013.01); *A61F 2/06* (2013.01); *A61B
2017/00526* (2013.01); *A61B 2017/00867*
(2013.01);
(Continued)

(58) Field of Classification Search
CPC ........ A61B 17/12113; A61B 17/12163; A61B
17/12172; A61B 17/12177; A61B
17/1219; A61B 17/12022; A61B
17/12027; A61B 17/12031; A61B
17/12099; A61B 17/12109; A61B
17/12122; A61B 17/1214; A61B
17/12168; A61B 17/12036; A61B
17/12118; A61B 17/12145; A61F 2/06;
A61F 2/82
See application file for complete search history.

(56) References Cited

U.S. PATENT DOCUMENTS 585,342 A 6/1897 Parrish
602,476 A 4/1898 Scott
(Continued)

FOREIGN PATENT DOCUMENTS

CA 2607529 A1 4/2008
CN 101472537 A 7/2009
(Continued)

*Primary Examiner* — Diane D Yabut
(74) *Attorney, Agent, or Firm* — Fortem IP LLP

(57) ABSTRACT

An aneurysm embolization device can include a body hav-
ing a single, continuous piece of material that is shape set
into a plurality of distinct structural components. For
example, the device can have an expandable component and
an atraumatic tip portion extending therefrom. Further, the
tip portion can be configured to enable the device to be
implanted within the aneurysm while tending to mitigate
risk of puncturing the aneurysm dome or otherwise assist in
framing the aneurysm in advance of placement of additional
embolic material.

15 Claims, 9 Drawing Sheets

Related U.S. Application Data continuation of application No. 16/523,131, filed on Jul. 26, 2019, now Pat. No. 11,389,309, which is a continuation of application No. 14/776,974, filed as application No. PCT/US2014/029613 on Mar. 14, 2014, now Pat. No. 10,736,758.

(60) Provisional application No. 61/789,423, filed on Mar. 15, 2013.

(51) Int. Cl.
| | | |
|---|---|---|
| *A61F 2/06* | (2013.01) | |
| *A61B 17/00* | (2006.01) | |

(52) U.S. Cl.
CPC . *A61B 2017/00898* (2013.01); *A61B 17/1219* (2013.01); *A61F 2002/823* (2013.01)

(56) References Cited

U.S. PATENT DOCUMENTS

| | | | |
|---|---|---|---|
| 618,349 | A | 1/1899 | Heany |
| 619,040 | A | 2/1899 | Haynes |
| 628,041 | A | 7/1899 | Schoenleber |
| 3,108,593 | A | 10/1963 | Glassman |
| 4,425,908 | A | 1/1984 | Simon |
| 4,619,246 | A | 10/1986 | Molgaard-Nielsen et al. |
| 4,655,771 | A | 4/1987 | Wallsten |
| 4,768,507 | A | 9/1988 | Fischell et al. |
| 4,921,484 | A | 5/1990 | Hillstead |
| 4,998,539 | A | 3/1991 | Delsanti |
| 5,026,377 | A | 6/1991 | Burton et al. |
| 5,061,275 | A | 10/1991 | Wallsten et al. |
| 5,064,435 | A | 11/1991 | Porter |
| 5,104,404 | A | 4/1992 | Wolff |
| 5,122,136 | A | 6/1992 | Guglielmi et al. |
| 5,158,548 | A | 10/1992 | Lau et al. |
| 5,222,971 | A | 6/1993 | Willard et al. |
| 5,250,071 | A | 10/1993 | Palermo |
| 5,308,356 | A | 5/1994 | Blackshear et al. |
| 5,334,210 | A | 8/1994 | Gianturco |
| 5,354,295 | A | 10/1994 | Guglielmi et al. |
| 5,378,239 | A | 1/1995 | Termin et al. |
| 5,405,379 | A | 4/1995 | Lane |
| 5,425,984 | A | 6/1995 | Kennedy et al. |
| 5,484,444 | A | 1/1996 | Braunschweiler et al. |
| 5,499,981 | A | 3/1996 | Kordis |
| 5,527,338 | A | 6/1996 | Purdy |
| 5,545,208 | A | 8/1996 | Wolff et al. |
| 5,545,209 | A | 8/1996 | Roberts et al. |
| 5,549,635 | A | 8/1996 | Solar |
| 5,624,461 | A | 4/1997 | Mariant |
| 5,634,942 | A | 6/1997 | Chevillon et al. |
| 5,645,558 | A | 7/1997 | Horton |
| 5,662,703 | A | 9/1997 | Yurek et al. |
| 5,669,931 | A | 9/1997 | Kupiecki et al. |
| 5,690,671 | A | 11/1997 | McGurk et al. |
| 5,702,419 | A | 12/1997 | Berry et al. |
| 5,713,907 | A | 2/1998 | Wholey et al. |
| 5,725,552 | A | 3/1998 | Kotula et al. |
| 5,728,906 | A | 3/1998 | Eguchi et al. |
| 5,733,294 | A | 3/1998 | Forber et al. |
| 5,741,333 | A | 4/1998 | Frid |
| 5,749,891 | A | 5/1998 | Ken et al. |
| 5,749,919 | A | 5/1998 | Blanc |
| 5,749,920 | A | 5/1998 | Quiachon et al. |
| 5,766,151 | A | 6/1998 | Valley et al. |
| 5,814,062 | A | 9/1998 | Sepetka et al. |
| 5,830,230 | A | 11/1998 | Berryman et al. |
| 5,846,261 | A | 12/1998 | Kotula et al. |
| 5,855,578 | A | 1/1999 | Guglielmi et al. |
| 5,879,366 | A | 3/1999 | Shaw et al. |
| 5,911,731 | A | 6/1999 | Pham et al. |
| 5,916,235 | A | 6/1999 | Guglielmi |
| 5,925,060 | A | 7/1999 | Forber |
| 5,928,228 | A | 7/1999 | Kordis et al. |
| 5,928,260 | A | 7/1999 | Chin et al. |
| 5,935,148 | A | 8/1999 | Mllar et al. |
| 5,935,362 | A | 8/1999 | Petrick |
| 5,941,249 | A | 8/1999 | Maynard |
| 5,944,738 | A | 8/1999 | Amplatz et al. |
| 5,951,599 | A | 9/1999 | McCrory |
| 5,957,948 | A | 9/1999 | Mariant |
| 5,976,162 | A | 11/1999 | Doan et al. |
| 5,980,554 | A | 11/1999 | Lenker et al. |
| 6,001,092 | A | 12/1999 | Mirigian et al. |
| 6,010,517 | A | 1/2000 | Baccaro |
| 6,033,423 | A | 3/2000 | Ken et al. |
| 6,036,720 | A | 3/2000 | Abrams et al. |
| 6,059,813 | A | 5/2000 | Vrba et al. |
| 6,063,070 | A | 5/2000 | Eder |
| 6,063,104 | A | 5/2000 | Mllar et al. |
| 6,086,577 | A | 7/2000 | Ken et al. |
| 6,093,199 | A | 7/2000 | Brown et al. |
| 6,096,034 | A | 8/2000 | Kupiecki et al. |
| 6,096,073 | A | 8/2000 | Webster et al. |
| 6,099,526 | A | 8/2000 | Whayne et al. |
| 6,106,530 | A | 8/2000 | Harada |
| 6,110,191 | A | 8/2000 | Dehdashtian et al. |
| 6,123,715 | A | 9/2000 | Amplatz |
| 6,139,564 | A | 10/2000 | Teoh |
| 6,152,144 | A | 11/2000 | Lesh et al. |
| 6,168,592 | B1 | 1/2001 | Kupiecki et al. |
| 6,168,615 | B1 | 1/2001 | Ken et al. |
| 6,168,618 | B1 | 1/2001 | Frantzen |
| 6,168,622 | B1 | 1/2001 | Mazzocchi |
| 6,171,326 | B1 | 1/2001 | Ferrera et al. |
| 6,193,708 | B1 | 2/2001 | Ken et al. |
| 6,221,086 | B1 | 4/2001 | Forber |
| 6,261,305 | B1 | 7/2001 | Marotta et al. |
| 6,306,141 | B1 | 10/2001 | Jervis |
| 6,309,367 | B1 | 10/2001 | Boock |
| 6,322,576 | B1 | 11/2001 | Wallace et al. |
| 6,325,820 | B1 | 12/2001 | Khosravi et al. |
| 6,331,184 | B1 | 12/2001 | Abrams |
| 6,332,576 | B1 | 12/2001 | Colley et al. |
| 6,342,068 | B1 | 1/2002 | Thompson |
| 6,344,041 | B1 | 2/2002 | Kupiecki et al. |
| 6,344,048 | B1 | 2/2002 | Chin et al. |
| 6,346,117 | B1 | 2/2002 | Greenhalgh |
| 6,350,270 | B1 | 2/2002 | Roue |
| 6,361,558 | B1 | 3/2002 | Hieshima et al. |
| 6,368,339 | B1 | 4/2002 | Amplatz |
| 6,375,668 | B1 | 4/2002 | Gifford et al. |
| 6,379,372 | B1 | 4/2002 | Dehdashtian et al. |
| 6,383,174 | B1 | 5/2002 | Eder |
| 6,391,037 | B1 | 5/2002 | Greenhalgh |
| 6,409,750 | B1 | 6/2002 | Hyodoh et al. |
| 6,428,558 | B1 | 8/2002 | Jones et al. |
| 6,443,972 | B1 | 9/2002 | Bosma et al. |
| 6,447,531 | B1 | 9/2002 | Amplatz |
| 6,454,780 | B1 | 9/2002 | Wallace |
| 6,506,204 | B2 | 1/2003 | Mazzocchi |
| 6,511,468 | B1 | 1/2003 | Cragg et al. |
| 6,530,934 | B1 | 3/2003 | Jacobsen et al. |
| 6,544,278 | B1 | 4/2003 | Vrba et al. |
| 6,547,804 | B2 | 4/2003 | Porter et al. |
| 6,551,303 | B1 | 4/2003 | Van et al. |
| 6,569,179 | B2 | 5/2003 | Teoh et al. |
| 6,579,302 | B2 | 6/2003 | Duerig et al. |
| 6,579,303 | B2 | 6/2003 | Amplatz |
| 6,585,748 | B1 | 7/2003 | Jeffree |
| 6,585,756 | B1 | 7/2003 | Strecker |
| 6,589,256 | B2 | 7/2003 | Forber |
| 6,589,265 | B1 | 7/2003 | Palmer et al. |
| 6,592,605 | B2 | 7/2003 | Lenker et al. |
| 6,599,308 | B2 | 7/2003 | Amplatz |
| 6,602,261 | B2 | 8/2003 | Greene et al. |
| 6,605,101 | B1 | 8/2003 | Schaefer et al. |
| 6,605,102 | B1 | 8/2003 | Mazzocchi et al. |
| 6,605,111 | B2 | 8/2003 | Bose et al. |
| 6,607,551 | B1 | 8/2003 | Sullivan et al. |
| 6,613,074 | B1 | 9/2003 | Mitelberg et al. |
| 6,626,939 | B1 | 9/2003 | Burnside et al. |

(56)                    References Cited

U.S. PATENT DOCUMENTS

| | | | |
|---|---|---|---|
| 6,632,241 | B1 | 10/2003 | Hancock et al. |
| 6,635,068 | B1 | 10/2003 | Dubrul et al. |
| 6,635,069 | B1 | 10/2003 | Teoh et al. |
| 6,652,555 | B1 | 11/2003 | Vantassel et al. |
| 6,652,556 | B1 | 11/2003 | Vantassel et al. |
| 6,666,882 | B1 | 12/2003 | Bose et al. |
| 6,666,883 | B1 | 12/2003 | Seguin et al. |
| 6,669,717 | B2 | 12/2003 | Marotta et al. |
| 6,669,721 | B1 | 12/2003 | Bose et al. |
| 6,676,696 | B1 | 1/2004 | Marotta et al. |
| 6,682,505 | B2 | 1/2004 | Bates et al. |
| 6,682,546 | B2 | 1/2004 | Amplatz |
| 6,689,150 | B1 | 2/2004 | Vantassel et al. |
| 6,689,486 | B2 | 2/2004 | Ho et al. |
| 6,695,876 | B1 | 2/2004 | Marotta et al. |
| 6,698,877 | B2 | 3/2004 | Urlaub et al. |
| 6,699,274 | B2 | 3/2004 | Stinson |
| 6,709,465 | B2 | 3/2004 | Mitchell et al. |
| 6,712,835 | B2 | 3/2004 | Mazzocchi et al. |
| 6,723,112 | B2 | 4/2004 | Ho et al. |
| 6,723,116 | B2 | 4/2004 | Taheri |
| 6,730,108 | B2 | 5/2004 | Van et al. |
| 6,746,468 | B1 | 6/2004 | Sepetka et al. |
| 6,746,890 | B2 | 6/2004 | Gupta et al. |
| 6,780,196 | B2 | 8/2004 | Chin et al. |
| 6,792,979 | B2 | 9/2004 | Konya et al. |
| 6,797,083 | B2 | 9/2004 | Peterson |
| 6,802,851 | B2 | 10/2004 | Jones et al. |
| RE38,653 | E | 11/2004 | Igaki et al. |
| 6,811,560 | B2 | 11/2004 | Jones et al. |
| 6,855,153 | B2 | 2/2005 | Saadat |
| 6,855,154 | B2 | 2/2005 | Abdel-Gawwad |
| RE38,711 | E | 3/2005 | Igaki et al. |
| 6,860,893 | B2 | 3/2005 | Wallace et al. |
| 6,878,384 | B2 | 4/2005 | Cruise et al. |
| 6,936,055 | B1 | 8/2005 | Ken et al. |
| 6,949,103 | B2 | 9/2005 | Mazzocchi et al. |
| 6,949,113 | B2 | 9/2005 | Van et al. |
| 6,953,472 | B2 | 10/2005 | Palmer et al. |
| 6,979,341 | B2 | 12/2005 | Scribner et al. |
| 6,989,019 | B2 | 1/2006 | Mazzocchi et al. |
| 6,994,092 | B2 | 2/2006 | Van et al. |
| 6,994,717 | B2 | 2/2006 | Konya et al. |
| 7,011,671 | B2 | 3/2006 | Welch |
| 7,018,401 | B1 | 3/2006 | Hyodoh et al. |
| 7,029,487 | B2 | 4/2006 | Greene et al. |
| 7,033,375 | B2 | 4/2006 | Mazzocchi et al. |
| 7,048,752 | B2 | 5/2006 | Mazzocchi et al. |
| 7,063,679 | B2 | 6/2006 | Maguire et al. |
| 7,070,607 | B2 | 7/2006 | Murayama et al. |
| 7,070,609 | B2 | 7/2006 | West |
| 7,083,632 | B2 | 8/2006 | Avellanet et al. |
| 7,128,073 | B1 | 10/2006 | Van et al. |
| 7,128,736 | B1 | 10/2006 | Abrams et al. |
| 7,169,177 | B2 | 1/2007 | Obara |
| 7,195,636 | B2 | 3/2007 | Avellanet et al. |
| 7,211,109 | B2 | 5/2007 | Thompson |
| 7,229,461 | B2 | 6/2007 | Chin et al. |
| 7,232,461 | B2 | 6/2007 | Ramer |
| 7,244,267 | B2 | 7/2007 | Huter et al. |
| 7,261,720 | B2 | 8/2007 | Stevens et al. |
| 7,303,571 | B2 | 12/2007 | Makower et al. |
| 7,306,622 | B2 | 12/2007 | Jones et al. |
| 7,331,980 | B2 | 2/2008 | Dubrul et al. |
| 7,367,985 | B2 | 5/2008 | Mazzocchi et al. |
| 7,367,986 | B2 | 5/2008 | Mazzocchi et al. |
| 7,371,250 | B2 | 5/2008 | Mazzocchi et al. |
| 7,393,358 | B2 | 7/2008 | Malewicz |
| 7,404,820 | B2 | 7/2008 | Mazzocchi et al. |
| 7,410,482 | B2 | 8/2008 | Murphy et al. |
| 7,410,492 | B2 | 8/2008 | Mazzocchi et al. |
| 7,413,622 | B2 | 8/2008 | Peterson |
| 7,419,503 | B2 | 9/2008 | Pulnev et al. |
| 7,442,200 | B2 | 10/2008 | Mazzocchi et al. |
| 7,485,088 | B2 | 2/2009 | Murphy et al. |
| 7,556,635 | B2 | 7/2009 | Mazzocchi et al. |
| 7,566,338 | B2 | 7/2009 | Mazzocchi et al. |
| 7,569,066 | B2 | 8/2009 | Gerberding et al. |
| 7,572,273 | B2 | 8/2009 | Mazzocchi et al. |
| 7,572,288 | B2 | 8/2009 | Cox |
| 7,575,590 | B2 | 8/2009 | Watson |
| 7,597,704 | B2 | 10/2009 | Frazier et al. |
| 7,601,160 | B2 | 10/2009 | Richter |
| 7,608,088 | B2 | 10/2009 | Jones et al. |
| 7,621,928 | B2 | 11/2009 | Thramann et al. |
| 7,632,296 | B2 | 12/2009 | Malewicz |
| 7,670,355 | B2 | 3/2010 | Mazzocchi et al. |
| 7,670,356 | B2 | 3/2010 | Mazzocchi et al. |
| 7,678,130 | B2 | 3/2010 | Mazzocchi et al. |
| 7,682,390 | B2 | 3/2010 | Seguin |
| 7,691,124 | B2 | 4/2010 | Balgobin |
| 7,695,488 | B2 | 4/2010 | Berenstein et al. |
| 7,699,056 | B2 | 4/2010 | Tran et al. |
| 7,727,189 | B2 | 6/2010 | Vantassel et al. |
| 7,744,583 | B2 | 6/2010 | Seifert et al. |
| 7,744,652 | B2 | 6/2010 | Morsi |
| 7,763,011 | B2 | 7/2010 | Ortiz et al. |
| 7,828,815 | B2 | 11/2010 | Mazzocchi et al. |
| 7,828,816 | B2 | 11/2010 | Mazzocchi et al. |
| 7,906,066 | B2 | 3/2011 | Wilson et al. |
| 7,922,732 | B2 | 4/2011 | Mazzocchi et al. |
| 7,955,343 | B2 | 6/2011 | Makower et al. |
| 7,972,359 | B2 | 7/2011 | Kreidler |
| RE42,625 | E | 8/2011 | Guglielmi |
| 7,993,364 | B2 | 8/2011 | Morsi |
| RE42,758 | E | 9/2011 | Ken et al. |
| 8,016,869 | B2 | 9/2011 | Nikolchev |
| 8,016,872 | B2 | 9/2011 | Parker |
| 8,043,326 | B2 | 10/2011 | Hancock et al. |
| 8,062,379 | B2 | 11/2011 | Morsi |
| 8,075,585 | B2 | 12/2011 | Lee et al. |
| 8,142,456 | B2 | 3/2012 | Rosqueta et al. |
| 8,202,280 | B2 | 6/2012 | Richter |
| 8,221,445 | B2 | 7/2012 | Van et al. |
| 8,261,648 | B1 | 9/2012 | Marchand et al. |
| 8,298,257 | B2 | 10/2012 | Sepetka et al. |
| 8,425,541 | B2 | 4/2013 | Masters et al. |
| 8,430,012 | B1 | 4/2013 | Marchand et al. |
| 8,454,681 | B2 | 6/2013 | Holman et al. |
| 8,470,013 | B2 | 6/2013 | Duggal et al. |
| 8,715,317 | B1 | 5/2014 | Janardhan et al. |
| 8,906,057 | B2 | 12/2014 | Connor et al. |
| 9,179,918 | B2 | 11/2015 | Levy et al. |
| 9,211,202 | B2 | 12/2015 | Strother et al. |
| 9,486,224 | B2 | 11/2016 | Riina et al. |
| 9,833,309 | B2 | 12/2017 | Levi et al. |
| 9,844,380 | B2 | 12/2017 | Furey |
| 9,907,684 | B2 | 3/2018 | Connor et al. |
| 9,962,146 | B2 | 5/2018 | Hebert et al. |
| 10,028,745 | B2 | 7/2018 | Morsi |
| 2001/0000797 | A1 | 5/2001 | Mazzocchi |
| 2001/0001835 | A1 | 5/2001 | Greene et al. |
| 2001/0007082 | A1 | 7/2001 | Dusbabek et al. |
| 2001/0012949 | A1 | 8/2001 | Forber |
| 2001/0051822 | A1 | 12/2001 | Stack et al. |
| 2002/0013599 | A1 | 1/2002 | Limon et al. |
| 2002/0013618 | A1 | 1/2002 | Marotta et al. |
| 2002/0042628 | A1 | 4/2002 | Chin et al. |
| 2002/0062091 | A1 | 5/2002 | Jacobsen et al. |
| 2002/0111647 | A1 | 8/2002 | Khairkhahan et al. |
| 2002/0165572 | A1 | 11/2002 | Saadat |
| 2002/0169473 | A1 | 11/2002 | Sepetka et al. |
| 2003/0004538 | A1 | 1/2003 | Secrest et al. |
| 2003/0018294 | A1 | 1/2003 | Cox |
| 2003/0028209 | A1 | 2/2003 | Teoh et al. |
| 2003/0040772 | A1 | 2/2003 | Hyodoh et al. |
| 2003/0057156 | A1 | 3/2003 | Peterson et al. |
| 2003/0171739 | A1 | 9/2003 | Murphy et al. |
| 2003/0171770 | A1 | 9/2003 | Kusleika et al. |
| 2003/0176884 | A1 | 9/2003 | Berrada et al. |
| 2003/0195553 | A1 | 10/2003 | Wallace et al. |
| 2003/0199913 | A1 | 10/2003 | Dubrul et al. |
| 2003/0199919 | A1 | 10/2003 | Palmer et al. |
| 2004/0015224 | A1 | 1/2004 | Armstrong et al. |

(56) References Cited

U.S. PATENT DOCUMENTS

| | | |
|---|---|---|
| 2004/0034386 A1 | 2/2004 | Fulton et al. |
| 2004/0044391 A1 | 3/2004 | Porter |
| 2004/0098027 A1 | 5/2004 | Teoh et al. |
| 2004/0098030 A1 | 5/2004 | Makower et al. |
| 2004/0106945 A1 | 6/2004 | Thramann et al. |
| 2004/0106977 A1 | 6/2004 | Sullivan et al. |
| 2004/0111112 A1 | 6/2004 | Hoffmann |
| 2004/0122467 A1 | 6/2004 | Vantassel et al. |
| 2004/0122468 A1 | 6/2004 | Yodfat et al. |
| 2004/0143239 A1 | 7/2004 | Zhou et al. |
| 2004/0143286 A1 | 7/2004 | Johnson et al. |
| 2004/0153119 A1 | 8/2004 | Kusleika et al. |
| 2004/0162606 A1 | 8/2004 | Thompson |
| 2004/0172056 A1 | 9/2004 | Guterman et al. |
| 2004/0172121 A1 | 9/2004 | Eidenschink et al. |
| 2004/0181253 A1 | 9/2004 | Sepetka et al. |
| 2004/0186562 A1 | 9/2004 | Cox |
| 2004/0193206 A1 | 9/2004 | Gerberding et al. |
| 2004/0215229 A1 | 10/2004 | Coyle |
| 2004/0215332 A1 | 10/2004 | Frid |
| 2004/0249408 A1 | 12/2004 | Murphy et al. |
| 2004/0267346 A1 | 12/2004 | Shelso |
| 2005/0010281 A1 | 1/2005 | Yodfat et al. |
| 2005/0021077 A1 | 1/2005 | Chin et al. |
| 2005/0033334 A1 | 2/2005 | Santra et al. |
| 2005/0033408 A1 | 2/2005 | Jones et al. |
| 2005/0033409 A1 | 2/2005 | Burke et al. |
| 2005/0043759 A1 | 2/2005 | Chanduszko |
| 2005/0060017 A1 | 3/2005 | Fischell et al. |
| 2005/0096728 A1 | 5/2005 | Ramer |
| 2005/0096732 A1 | 5/2005 | Marotta et al. |
| 2005/0107823 A1 | 5/2005 | Leone et al. |
| 2005/0131443 A1 | 6/2005 | Abdel-Gawwad |
| 2005/0192619 A1 | 9/2005 | Teoh et al. |
| 2005/0222605 A1 | 10/2005 | Greenhalgh et al. |
| 2005/0228434 A1 | 10/2005 | Amplatz et al. |
| 2005/0267511 A1 | 12/2005 | Marks et al. |
| 2005/0267568 A1 | 12/2005 | Berez et al. |
| 2005/0273135 A1 | 12/2005 | Chanduszko et al. |
| 2005/0288763 A1 | 12/2005 | Andreas et al. |
| 2006/0052816 A1 | 3/2006 | Bates et al. |
| 2006/0064151 A1 | 3/2006 | Guterman et al. |
| 2006/0074475 A1 | 4/2006 | Gumm |
| 2006/0106421 A1 | 5/2006 | Teoh |
| 2006/0116713 A1 | 6/2006 | Sepetka et al. |
| 2006/0116714 A1 | 6/2006 | Sepetka et al. |
| 2006/0155323 A1 | 7/2006 | Porter et al. |
| 2006/0167494 A1 | 7/2006 | Suddaby |
| 2006/0190070 A1 | 8/2006 | Dieck et al. |
| 2006/0190076 A1 | 8/2006 | Taheri |
| 2006/0200221 A1 | 9/2006 | Malewicz |
| 2006/0200234 A1 | 9/2006 | Hines |
| 2006/0206199 A1 | 9/2006 | Churchwell et al. |
| 2006/0206200 A1 | 9/2006 | Garcia et al. |
| 2006/0217799 A1 | 9/2006 | Mailänder et al. |
| 2006/0229700 A1 | 10/2006 | Acosta et al. |
| 2006/0235464 A1 | 10/2006 | Avellanet et al. |
| 2006/0235501 A1 | 10/2006 | Igaki |
| 2006/0241690 A1 | 10/2006 | Amplatz et al. |
| 2006/0247680 A1 | 11/2006 | Amplatz et al. |
| 2006/0264905 A1 | 11/2006 | Eskridge et al. |
| 2006/0264907 A1 | 11/2006 | Eskridge et al. |
| 2006/0271149 A1 | 11/2006 | Berez et al. |
| 2006/0271153 A1 | 11/2006 | Garcia et al. |
| 2006/0276827 A1 | 12/2006 | Mitelberg et al. |
| 2006/0282152 A1 | 12/2006 | Beyerlein et al. |
| 2006/0292206 A1 | 12/2006 | Kim et al. |
| 2006/0293744 A1 | 12/2006 | Peckham et al. |
| 2007/0005125 A1 | 1/2007 | Berenstein et al. |
| 2007/0016243 A1 | 1/2007 | Ramaiah et al. |
| 2007/0021816 A1 | 1/2007 | Rudin |
| 2007/0050017 A1 | 3/2007 | Sims et al. |
| 2007/0088387 A1 | 4/2007 | Eskridge et al. |
| 2007/0093889 A1 | 4/2007 | Wu et al. |
| 2007/0100415 A1 | 5/2007 | Licata et al. |
| 2007/0100426 A1 | 5/2007 | Rudakov et al. |
| 2007/0106311 A1 | 5/2007 | Wallace et al. |
| 2007/0135826 A1 | 6/2007 | Zaver et al. |
| 2007/0150045 A1 | 6/2007 | Ferrera |
| 2007/0162104 A1 | 7/2007 | Frid |
| 2007/0173928 A1 | 7/2007 | Morsi |
| 2007/0175536 A1 | 8/2007 | Monetti et al. |
| 2007/0191884 A1 | 8/2007 | Eskridge et al. |
| 2007/0191924 A1 | 8/2007 | Rudakov |
| 2007/0198075 A1 | 8/2007 | Levy |
| 2007/0203567 A1 | 8/2007 | Levy |
| 2007/0219619 A1 | 9/2007 | Dieck et al. |
| 2007/0221230 A1 | 9/2007 | Thompson et al. |
| 2007/0225760 A1 | 9/2007 | Moszner et al. |
| 2007/0225794 A1 | 9/2007 | Thramann et al. |
| 2007/0233224 A1 | 10/2007 | Leynov et al. |
| 2007/0233244 A1 | 10/2007 | Lopez et al. |
| 2007/0239261 A1 | 10/2007 | Bose et al. |
| 2007/0265656 A1 | 11/2007 | Amplatz et al. |
| 2007/0270902 A1 | 11/2007 | Slazas et al. |
| 2007/0288083 A1 | 12/2007 | Hines |
| 2007/0293935 A1 | 12/2007 | Olsen et al. |
| 2008/0009934 A1 | 1/2008 | Schneider et al. |
| 2008/0021535 A1 | 1/2008 | Leopold et al. |
| 2008/0039933 A1 | 2/2008 | Yodfat et al. |
| 2008/0045996 A1 | 2/2008 | Makower et al. |
| 2008/0045997 A1 | 2/2008 | Balgobin et al. |
| 2008/0051705 A1 | 2/2008 | Von et al. |
| 2008/0058856 A1 | 3/2008 | Ramaiah et al. |
| 2008/0065141 A1 | 3/2008 | Holman et al. |
| 2008/0065145 A1 | 3/2008 | Carpenter |
| 2008/0097495 A1 | 4/2008 | Feller et al. |
| 2008/0109063 A1 | 5/2008 | Hancock et al. |
| 2008/0114391 A1 | 5/2008 | Dieck et al. |
| 2008/0114436 A1 | 5/2008 | Dieck et al. |
| 2008/0114439 A1 | 5/2008 | Ramaiah et al. |
| 2008/0119886 A1 | 5/2008 | Greenhalgh et al. |
| 2008/0125806 A1 | 5/2008 | Mazzocchi et al. |
| 2008/0125848 A1 | 5/2008 | Kusleika et al. |
| 2008/0132989 A1 | 6/2008 | Snow et al. |
| 2008/0140177 A1 | 6/2008 | Hines |
| 2008/0154286 A1 | 6/2008 | Abbott et al. |
| 2008/0195139 A1 | 8/2008 | Donald et al. |
| 2008/0219533 A1 | 9/2008 | Grigorescu |
| 2008/0221600 A1 | 9/2008 | Dieck et al. |
| 2008/0243226 A1 | 10/2008 | Fernandez et al. |
| 2008/0249562 A1 | 10/2008 | Cahill |
| 2008/0262598 A1 | 10/2008 | Elmaleh |
| 2008/0281350 A1 | 11/2008 | Sepetka et al. |
| 2008/0319533 A1 | 12/2008 | Lehe |
| 2009/0025820 A1 | 1/2009 | Adams |
| 2009/0069806 A1 | 3/2009 | De et al. |
| 2009/0082803 A1 | 3/2009 | Adams et al. |
| 2009/0099647 A1 | 4/2009 | Glimsdale et al. |
| 2009/0112251 A1 | 4/2009 | Qian et al. |
| 2009/0118811 A1 | 5/2009 | Moloney |
| 2009/0125094 A1 | 5/2009 | Rust |
| 2009/0143849 A1 | 6/2009 | Ozawa et al. |
| 2009/0143851 A1 | 6/2009 | Paul |
| 2009/0198315 A1 | 8/2009 | Boudjemline |
| 2009/0204145 A1 | 8/2009 | Matthews |
| 2009/0210047 A1 | 8/2009 | Amplatz et al. |
| 2009/0216307 A1 | 8/2009 | Kaufmann et al. |
| 2009/0228029 A1 | 9/2009 | Lee |
| 2009/0228093 A1 | 9/2009 | Taylor et al. |
| 2009/0259202 A1 | 10/2009 | Leeflang et al. |
| 2009/0264914 A1 | 10/2009 | Riina et al. |
| 2009/0275974 A1 | 11/2009 | Marchand et al. |
| 2009/0287291 A1 | 11/2009 | Becking et al. |
| 2009/0287294 A1 | 11/2009 | Rosqueta et al. |
| 2009/0287297 A1 | 11/2009 | Cox |
| 2009/0318941 A1 | 12/2009 | Sepetka et al. |
| 2009/0318948 A1 | 12/2009 | Davis et al. |
| 2010/0004726 A1 | 1/2010 | Hancock et al. |
| 2010/0004761 A1 | 1/2010 | Flanders et al. |
| 2010/0023048 A1 | 1/2010 | Mach |
| 2010/0023105 A1 | 1/2010 | Levy et al. |
| 2010/0030220 A1 | 2/2010 | Truckai et al. |
| 2010/0036390 A1 | 2/2010 | Gumm |

(56)  References Cited

U.S. PATENT DOCUMENTS

| | | |
|---|---|---|
| 2010/0042133 A1 | 2/2010 | Ramzipoor et al. |
| 2010/0069948 A1 | 3/2010 | Veznedaroglu et al. |
| 2010/0087908 A1 | 4/2010 | Hilaire et al. |
| 2010/0094335 A1 | 4/2010 | Gerberding et al. |
| 2010/0131002 A1 | 5/2010 | Connor et al. |
| 2010/0144895 A1 | 6/2010 | Porter |
| 2010/0152767 A1 | 6/2010 | Greenhalgh et al. |
| 2010/0185271 A1 | 7/2010 | Zhang |
| 2010/0222802 A1 | 9/2010 | Gillespie et al. |
| 2010/0249894 A1 | 9/2010 | Oba et al. |
| 2010/0256667 A1 | 10/2010 | Ashby et al. |
| 2010/0268260 A1 | 10/2010 | Riina et al. |
| 2010/0274276 A1 | 10/2010 | Chow et al. |
| 2010/0312270 A1 | 12/2010 | McGuckin et al. |
| 2010/0331948 A1 | 12/2010 | Turovskiy et al. |
| 2011/0022149 A1 | 1/2011 | Cox et al. |
| 2011/0054519 A1 | 3/2011 | Neuss |
| 2011/0082493 A1 | 4/2011 | Samson et al. |
| 2011/0106234 A1 | 5/2011 | Grandt |
| 2011/0137405 A1 | 6/2011 | Wilson et al. |
| 2011/0144669 A1 | 6/2011 | Becking et al. |
| 2011/0152993 A1 | 6/2011 | Marchand et al. |
| 2011/0184452 A1 | 7/2011 | Huynh et al. |
| 2011/0184453 A1 | 7/2011 | Levy et al. |
| 2011/0196415 A1 | 8/2011 | Ujiie et al. |
| 2011/0202085 A1 | 8/2011 | Loganathan et al. |
| 2011/0208227 A1 | 8/2011 | Becking |
| 2011/0245862 A1 | 10/2011 | Dieck et al. |
| 2011/0265943 A1 | 11/2011 | Rosqueta et al. |
| 2011/0276120 A1 | 11/2011 | Gilson et al. |
| 2011/0313447 A1 | 12/2011 | Strauss et al. |
| 2011/0319926 A1 | 12/2011 | Becking et al. |
| 2012/0041470 A1 | 2/2012 | Shrivastava et al. |
| 2012/0065720 A1 | 3/2012 | Strauss et al. |
| 2012/0101561 A1 | 4/2012 | Porter |
| 2012/0143237 A1 | 6/2012 | Cam et al. |
| 2012/0143317 A1 | 6/2012 | Cam et al. |
| 2012/0165803 A1 | 6/2012 | Bencini et al. |
| 2012/0165919 A1 | 6/2012 | Cox et al. |
| 2012/0197283 A1 | 8/2012 | Marchand et al. |
| 2012/0226343 A1 | 9/2012 | Vo et al. |
| 2012/0239074 A1 | 9/2012 | Aboytes et al. |
| 2012/0245674 A1 | 9/2012 | Molaei et al. |
| 2012/0245675 A1 | 9/2012 | Molaei et al. |
| 2012/0283768 A1 | 11/2012 | Cox et al. |
| 2012/0316598 A1 | 12/2012 | Becking et al. |
| 2012/0316632 A1 | 12/2012 | Gao |
| 2012/0330341 A1 | 12/2012 | Becking et al. |
| 2012/0330347 A1 | 12/2012 | Becking et al. |
| 2013/0018451 A1 | 1/2013 | Grabowski et al. |
| 2013/0066357 A1 | 3/2013 | Aboytes et al. |
| 2013/0066360 A1 | 3/2013 | Becking et al. |
| 2013/0085522 A1 | 4/2013 | Becking et al. |
| 2013/0092013 A1 | 4/2013 | Thompson et al. |
| 2013/0123830 A1 | 5/2013 | Becking et al. |
| 2013/0211495 A1 | 8/2013 | Halden et al. |
| 2013/0233160 A1 | 9/2013 | Marchand et al. |
| 2013/0239790 A1 | 9/2013 | Thompson et al. |
| 2013/0245667 A1 | 9/2013 | Marchand et al. |
| 2013/0245670 A1 | 9/2013 | Fan |
| 2013/0268053 A1 | 10/2013 | Molaei et al. |
| 2013/0274862 A1 | 10/2013 | Cox et al. |
| 2013/0274863 A1 | 10/2013 | Cox et al. |
| 2013/0274866 A1 | 10/2013 | Cox et al. |
| 2013/0274868 A1 | 10/2013 | Cox et al. |
| 2013/0304179 A1 | 11/2013 | Bialas et al. |
| 2013/0345739 A1 | 12/2013 | Brady et al. |
| 2014/0005713 A1 | 1/2014 | Bowman |
| 2014/0005714 A1 | 1/2014 | Quick et al. |
| 2014/0012307 A1 | 1/2014 | Franano et al. |
| 2014/0058420 A1 | 2/2014 | Hannes et al. |
| 2014/0128905 A1 | 5/2014 | Molaei |
| 2014/0172001 A1 | 6/2014 | Becking et al. |
| 2014/0200648 A1 | 7/2014 | Newell et al. |
| 2014/0277361 A1 | 9/2014 | Farhat et al. |
| 2014/0316012 A1 | 10/2014 | Freyman et al. |
| 2014/0371734 A1 | 12/2014 | Truckai |
| 2015/0157331 A1 | 6/2015 | Levy et al. |
| 2015/0216684 A1 | 8/2015 | Enzmann et al. |
| 2015/0245932 A1 | 9/2015 | Molaei et al. |
| 2015/0250628 A1 | 9/2015 | Monstadt et al. |
| 2015/0313737 A1 | 11/2015 | Tippett et al. |
| 2015/0327843 A1 | 11/2015 | Garrison |
| 2016/0066921 A1 | 3/2016 | Seifert et al. |
| 2016/0135984 A1 | 5/2016 | Rudakov et al. |
| 2016/0206320 A1 | 7/2016 | Connor |
| 2016/0206321 A1 | 7/2016 | Connor |
| 2016/0249934 A1 | 9/2016 | Hewitt et al. |
| 2017/0150971 A1 | 6/2017 | Hines |
| 2017/0156903 A1 | 6/2017 | Shobayashi |
| 2017/0189035 A1 | 7/2017 | Porter |
| 2017/0266023 A1 | 9/2017 | Thomas |
| 2017/0340333 A1 | 11/2017 | Badruddin et al. |
| 2017/0367708 A1 | 12/2017 | Mayer et al. |
| 2018/0049859 A1 | 2/2018 | Stoppenhagen et al. |
| 2018/0125686 A1 | 5/2018 | Lu |
| 2018/0140305 A1 | 5/2018 | Connor |
| 2018/0161185 A1 | 6/2018 | Kresslein et al. |
| 2018/0193025 A1 | 7/2018 | Walzman |
| 2018/0193026 A1 | 7/2018 | Yang et al. |
| 2018/0206852 A1 | 7/2018 | Moeller |
| 2019/0053811 A1 | 2/2019 | Garza et al. |
| 2019/0343664 A1 | 11/2019 | Ruvalcaba et al. |
| 2022/0304835 A1 | 9/2022 | Ruvalcaba et al. |

FOREIGN PATENT DOCUMENTS

| | | |
|---|---|---|
| DE | 1283434 B | 11/1968 |
| DE | 102008028308 A1 | 4/2009 |
| DE | 102010050569 A1 | 5/2012 |
| DE | 102011011510 A1 | 8/2012 |
| EP | 1621148 A1 | 2/2006 |
| EP | 1637176 A1 | 3/2006 |
| EP | 1752112 A1 | 2/2007 |
| EP | 1942972 A1 | 7/2008 |
| EP | 1872742 B1 | 5/2009 |
| EP | 2279023 A2 | 2/2011 |
| EP | 2363075 A1 | 9/2011 |
| EP | 2496299 A2 | 9/2012 |
| EP | 2675402 A2 | 12/2013 |
| FR | 2556210 B1 | 4/1988 |
| FR | 2890306 A1 | 3/2007 |
| JP | 11506686 | 6/1999 |
| JP | 2003520103 A | 7/2003 |
| JP | 2003524434 A | 8/2003 |
| JP | 2004049585 A | 2/2004 |
| JP | 2005522266 A | 7/2005 |
| JP | 2006506201 A | 2/2006 |
| JP | 2008541832 A | 11/2008 |
| JP | 4673987 B2 | 1/2011 |
| WO | 8800813 A1 | 2/1988 |
| WO | 9601591 A1 | 1/1996 |
| WO | 9726939 A1 | 7/1997 |
| WO | 9903404 A1 | 1/1999 |
| WO | 9905977 A1 | 2/1999 |
| WO | 9908607 A1 | 2/1999 |
| WO | 9908743 A1 | 2/1999 |
| WO | 9940873 A1 | 8/1999 |
| WO | 9962432 A1 | 12/1999 |
| WO | 2005117718 A1 | 12/2005 |
| WO | 2006026744 A1 | 3/2006 |
| WO | 2006034166 A2 | 3/2006 |
| WO | 2006052322 A2 | 5/2006 |
| WO | 2006091891 A2 | 8/2006 |
| WO | 2006119422 A2 | 11/2006 |
| WO | 2007047851 A2 | 4/2007 |
| WO | 2007076480 A2 | 7/2007 |
| WO | 2007095031 A2 | 8/2007 |
| WO | 2007121405 A2 | 10/2007 |
| WO | 2008022327 A2 | 2/2008 |
| WO | 2008151204 A1 | 12/2008 |
| WO | 2008157507 A2 | 12/2008 |
| WO | 2009076515 A1 | 6/2009 |
| WO | 2009132045 A2 | 10/2009 |

(56)     References Cited

FOREIGN PATENT DOCUMENTS

| | | | |
|---|---|---|---|
| WO | 2009134337 | A1 | 11/2009 |
| WO | 2009135166 | A2 | 11/2009 |
| WO | 2010028314 | A1 | 3/2010 |
| WO | 2010030991 | A1 | 3/2010 |
| WO | 2010147808 | A1 | 12/2010 |
| WO | 2011057002 | A2 | 5/2011 |
| WO | 2011057277 | A2 | 5/2011 |
| WO | 2011066962 | A1 | 6/2011 |
| WO | 2011130081 | A1 | 10/2011 |
| WO | 2011153304 | A1 | 12/2011 |
| WO | 2012068175 | A2 | 5/2012 |
| WO | 2012112749 | A2 | 8/2012 |
| WO | 2012166804 | A1 | 12/2012 |
| WO | 2017074411 | A1 | 5/2017 |
| WO | 2018051187 | A1 | 3/2018 |

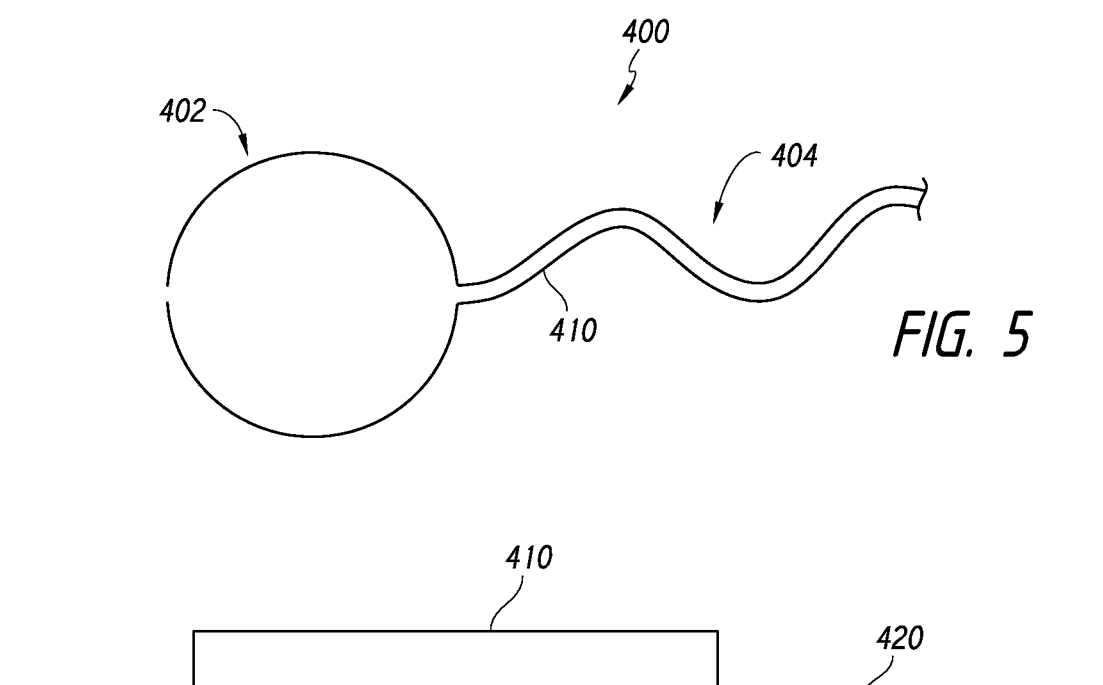
*FIG. 5*
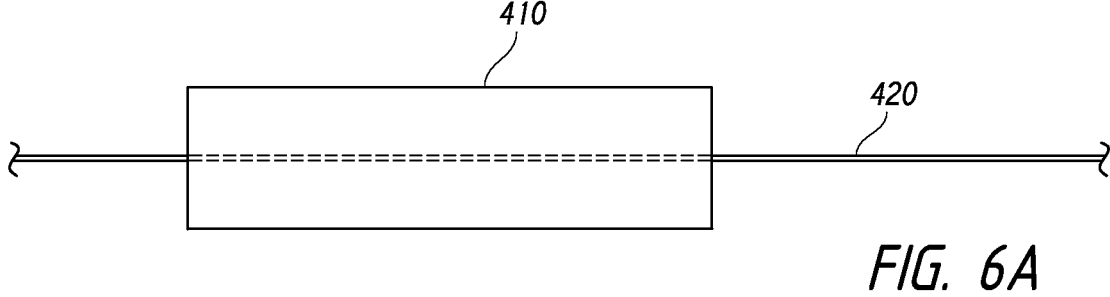
*FIG. 6A*
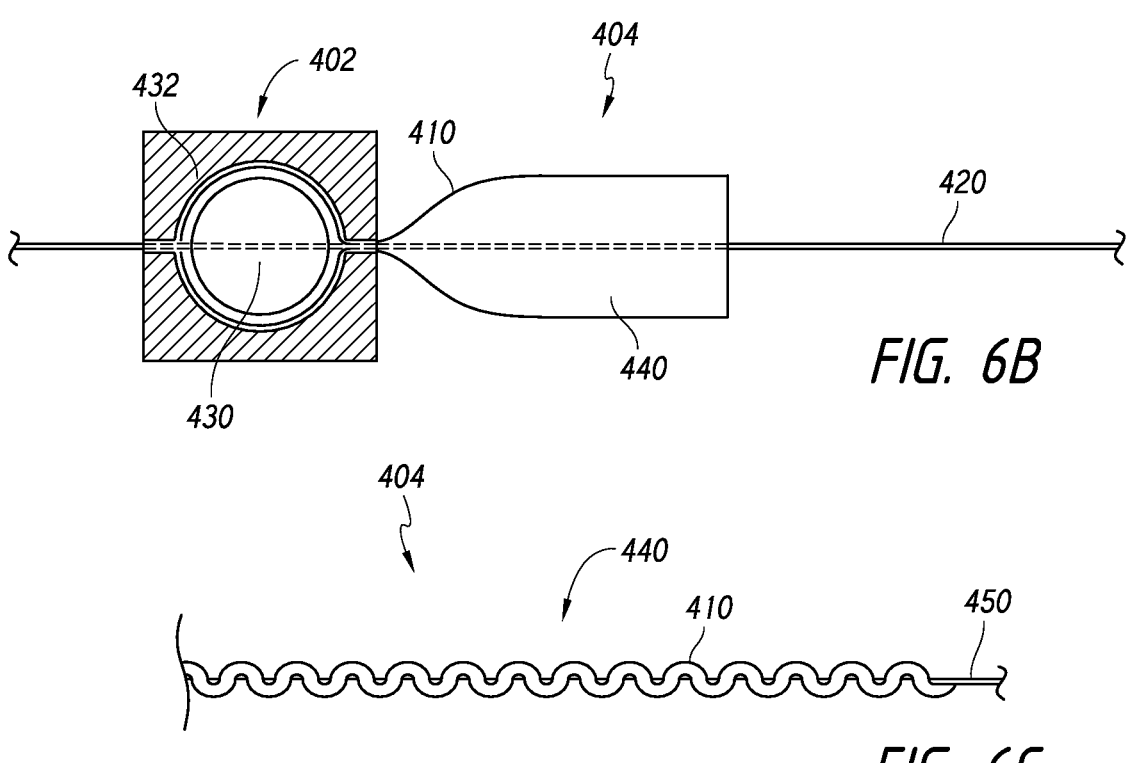
*FIG. 6B*
*FIG. 6C*

OCCLUSIVE DEVICE

CROSS-REFERENCE TO RELATED APPLICATIONS

This application is a continuation of U.S. patent application Ser. No. 17/807,025, filed Jun. 15, 2022, which is a continuation of U.S. patent application Ser. No. 16/523,131, filed Jul. 26, 2019, now U.S. Pat. No. 11,389,309, which is a continuation of U.S. patent application Ser. No. 14/776, 974, filed Sep. 15, 2015, now U.S. Pat. No. 10,736,758, which is the National Stage Application of International Application No. PCT/US2014/029613, filed Mar. 14, 2014, which claims the priority benefit of U.S. Provisional Application No. 61/789,423, filed Mar. 15, 2013, the entireties of all of which are incorporated herein by reference.

FIELD OF THE INVENTIONS

The present inventions relate to implantable devices. More specifically, the present inventions relate to occlusive devices that can be implanted intravenously, and in some embodiments, for aneurysm therapy.

DESCRIPTION OF THE RELATED ART

Walls of the vasculature, particularly arterial walls, may develop areas of pathological dilatation called aneurysms. As is well known, aneurysms have thin, weak walls that are prone to rupturing. Aneurysms can be the result of the vessel wall being weakened by disease, injury or a congenital abnormality. Aneurysms could be found in different parts of the body with the most common being abdominal aortic aneurysms and brain or cerebral aneurysms in the neurovasculature. When the weakened wall of an aneurysm ruptures, it can result in death, especially if it is a cerebral aneurysm that ruptures.

Aneurysms are generally treated by excluding the weakened part of the vessel from the arterial circulation. For treating a cerebral aneurysm, such reinforcement is done in many ways including: (i) surgical clipping, where a metal clip is secured around the base of the aneurysm; (ii) packing the aneurysm with small, flexible wire coils (micro-coils); (iii) using embolic materials to "fill" or "pack" an aneurysm; (iv) using detachable balloons or coils to occlude the parent vessel that supplies the aneurysm; and (v) intravascular stenting.

In conventional methods of introducing a compressed stent into a vessel and positioning it within in an area of stenosis or an aneurysm, a guiding catheter having a distal tip is percutaneously introduced into the vascular system of a patient. The guiding catheter is advanced within the vessel until its distal tip is proximate the stenosis or aneurysm. A guidewire positioned within an inner lumen of a second, inner catheter and the inner catheter are advanced through the distal end of the guiding catheter. The guidewire is then advanced out of the distal end of the guiding catheter into the vessel until the distal portion of the guidewire carrying the compressed stent is positioned at the point of the lesion within the vessel. Once the compressed stent is located at the lesion, the stent may be released and expanded so that it supports the vessel.

Numerous companies have pursued ball-type embolization devices for aneurysm treatment. Generally, braid-ball embolic devices for aneurysm treatment and/or other types of embolization operate through blood flow disruption and subsequent thrombus formation.

The braid density of the device has an effect on blood flow through the device. Greater braid density in the implant results in greater flow disruption, less time to occlusion, and/or improved likelihood of durable occlusion. The size of microcatheter through which the device can be tracked to achieve endovascular access sets the primary limitation on the amount of braid (i.e., size and number of filaments) that may be included in the device. Device configuration for tracking then becomes the remaining design variable that can be leveraged to achieve desired performance.

SUMMARY

Systems and procedures for treating aneurysms can include an embolization device having one or more expandable components that can be inserted into an aneurysm to facilitate a thrombotic, healing effect. The components can have distinct and specific characteristics, including porosity, composition, material, shape, size, coating, and the like. These characteristics can be selected in order to achieve a desired treatment or placement of the device.

In accordance with some embodiments, the device can comprise at least two sections formed from a single, continuous piece of material that is shape set such that the sections comprise different shapes or sizes. In some embodiments, a first of the sections can serve a first function and a second of the sections can serve a second function. The first function can include mitigating migration of components or sections of the device, ensuring that the device doesn't pierce the aneurysm wall, providing a frame for the device, or other support or structural functions for device operation. The second function can entail filling the volume of the aneurysm, whether with single or multiple interconnected components. When being placed, the first function can be performed before or after the second function. Accordingly, the first section can be placed into the aneurysm before, after, or concurrently with the second section.

For example, the first section can function as an atraumatic tip portion that can be placed into an aneurysm before the second portion, providing the second portion a "nest" or cushion when received within the aneurysm. Further, the first section can comprise a framing member into which the second section can be inserted. Accordingly, in some embodiments, the first and second sections can have functions that are interrelated or complimentary. Thus, some embodiments of the device can advantageously integrate multiple components into a device comprising a single, continuous piece of material that provides dynamic and complex functionality.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1 or clause 5. The other clauses can be presented in a similar manner.

Clause 1. An aneurysm embolization device, comprising: a body portion having a first end and being self-expandable to a first expanded configuration; and an atraumatic tip portion extending from the first end and being self-expandable to a second expanded configuration, different from the first expanded configuration; wherein the body portion and the tip portion comprise a single, continuous piece of material. The second configuration can be different in shape or size from the first expanded configuration.

Clause 2. The device of Clause 1, wherein in the device further comprises a lumen extending continuously through the body portion and the tip portion.

Clause 3. The device of Clause 2, wherein the lumen comprises a non-zero diameter in the first expanded configuration of the body portion and a substantially zero cross-sectional dimension in the second expanded configuration of the tip portion. The cross-sectional dimension can comprise a diameter or width of the lumen.

Clause 4. The device of any of Clauses 2 to 3, wherein the lumen in the body portion expands when the body portion is released from a compressed state.

Clause 5. The device of any of Clauses 2 to 4, wherein the lumen diameter in the body portion varies along a longitudinal length of the body portion in the first expanded configuration.

Clause 6. The device of any of Clauses 1 to 5, wherein in a compressed state, the body portion and the tip portion comprise an outer diameter of between about 0.010" and about 0.050".

Clause 7. The device of any of Clauses 1 to 6, wherein in a compressed state, the body portion and the tip portion comprise an outer diameter of between about 0.015" and about 0.030".

Clause 8. The device of any of Clauses 1 to 7, wherein in a compressed state, the body portion and the tip portion comprise an outer diameter of between about 0.020" and about 0.025".

Clause 9. The device of any of Clauses 1 to 8, wherein in the second expanded configuration, a lumen of the tip portion comprises an inner diameter of between about 0.010" and about 0.050".

Clause 10. The device of any of Clauses 1 to 9, wherein in the second expanded configuration, a lumen of the tip portion comprises an inner diameter of between about 0.015" and about 0.030".

Clause 11. The device of any of Clauses 1 to 10, wherein in the second expanded configuration, a lumen of the tip portion comprises an inner diameter of between about 0.020" and about 0.025".

Clause 12. The device of any of Clauses 1 to 11, wherein in the first expanded configuration, a lumen of the body portion comprises a maximum inner diameter of between about 0.080" and about 0.250".

Clause 13. The device of any of Clauses 1 to 12, wherein the tip portion is shape-set as a helical member.

Clause 14. The device of any of Clauses 1 to 13, wherein the piece of material comprises a tubular material.

Clause 15. The device of any of Clauses 1 to 14, wherein the piece of material comprises a braided material.

Clause 16. The device of any of Clauses 1 to 15, wherein the body portion comprises a single layer of braided filaments.

Clause 17. The device of any of Clauses 1 to 16, wherein the body portion comprises a dual layer of braided filaments.

Clause 18. The device of any of Clauses 1 to 17, wherein the body portion comprises a folded end, opposite the first end, whereat the layers of braided filaments meet.

Clause 19. The device of any of Clauses 1 to 18, wherein the piece of material is folded onto itself along the body portion.

Clause 20. The device of any of Clauses 1 to 19, wherein the piece of material comprises a first end positioned at a free end of the tip portion, opposite the body portion first end, the piece of material being folded onto itself along the body portion.

Clause 21. The device of Clause 20, wherein the piece of material comprises a second end positioned at the body portion first end.

Clause 22. The device of Clause 20, wherein the piece of material is folded onto itself along the body portion and the tip portion.

Clause 23. The device any of Clauses 1 to 22, wherein the expandable body portion comprises a cup shape.

Clause 24. The device of any of Clauses 1 to 23, wherein the expandable body portion comprises a disc shape.

Clause 25. The device of any of Clauses 1 to 24, wherein the expandable body portion comprises a closed, rounded three-dimensional shape.

Clause 26. The device of Clause 25, wherein the closed, rounded three-dimensional shape comprises a solid of revolution, a spheroid, or an ellipsoid.

Clause 27. The device of any of Clauses 1 to 26, wherein the body portion comprises a plurality of expandable members.

Clause 28. The device of Clause 27, wherein the plurality of expandable members comprises closed, rounded three-dimensional shapes.

Clause 29. The device of any of Clauses 1 to 28, wherein the tip portion is shape-set such that the second expanded configuration comprises a hollow cage shape.

Clause 30. The device of any of Clauses 1 to 29, further comprising a hub coupled to the device at the first end.

Clause 31. The device of Clause 30, wherein the body portion converges to a substantially zero dimension at the hub.

Clause 32. An aneurysm embolization device, comprising: a tubular body having first and second portions being self-expandable from a first cross-sectional dimension, the first portion being expandable to an expanded cross-sectional dimension greater than an expanded cross-sectional dimension of the second portion, the first portion expanding to a globular shape and the second portion extending away from the first portion in a substantially helical path. The cross-sectional dimensions can comprise a diameter or width.

Clause 33. The device of Clause 32, wherein the second portion is shape-set to substantially the first cross-sectional dimension and a longitudinal axis of the second portion extends along the substantially helical path.

Clause 34. The device of any of Clauses 32 to 33, wherein the body comprises a tubular braid.

Clause 35. The device of any of Clauses 32 to 34, wherein the first and second portions are formed from a single, continuous tubular braid.

Clause 36. The device of any of Clauses 32 to 35, further comprising a hub coupled to the device at a midsection between the first and second portions.

Clause 37. A method of manufacturing an aneurysm embolization device, comprising: shape-setting a body portion of a device to a first shape; shape-setting a tip portion of the device to a second shape, different than the first shape, the tip portion and body portion being a single, continuous piece of material; wherein the body portion and the tip portion are self-expandable from a first configuration to the respective first and second shapes.

Clause 38. The method of Clause 37, wherein the shape-setting a body portion comprises positioning the body portion around a form.

Clause 39. The method of any of Clauses 37 to 38, wherein the shape-setting a body portion comprises inserting a form into a tubular material.

Clause 40. The method of any of Clauses 37 to 39, wherein the shape-setting a body portion comprises setting the first shape to a cup shape.

Clause 41. The method of any of Clauses 37 to 40, wherein the shape-setting a body portion comprises setting the first shape to a disc shape.

Clause 42. The method of any of Clauses 37 to 41, wherein the shape-setting a body portion comprises setting the first shape to a closed, rounded three-dimensional shape.

Clause 43. The method of Clause 42, wherein the closed, rounded three-dimensional shape comprises a solid of revolution, a spheroid, or an ellipsoid.

Clause 44. The method of any of Clauses 37 to 43, wherein the shape-setting a body portion comprises setting the first shape to a plurality of expandable members.

Clause 45. The method of Clause 44, wherein the plurality of expandable members comprises closed, rounded three-dimensional shapes.

Clause 46. The method of any of Clauses 37 to 45, wherein the shape-setting a tip portion comprises setting the second shape to a helical shape.

Clause 47. The method of Clause 46, wherein the shape-setting a tip portion comprises winding the tip portion around a mandrel.

Clause 48. The method of any of Clauses 37 to 47, wherein the shape-setting a tip portion comprises setting the second shape to a hollow cage.

Clause 49. The method of any of Clauses 37 to 48, further comprising everting a tubular material of the device such that the body portion comprises a dual layer of material.

Clause 50. The method of Clause 49, wherein the everting comprises positioning a first end of the tubular material adjacent to a midsection between the body portion and the tip portion.

Clause 51. The method of any of Clauses 37 to 50, wherein the piece of material comprises a tubular braid.

Clause 52. The method of Clause 51, further comprising removing filaments of the tubular braid from the tip portion.

Clause 53. An aneurysm embolization device, comprising any combination of the features disclosed herein.

Clause 54. A method of manufacturing any of the aneurysm embolization devices disclosed herein using any of the steps disclosed herein.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

Various features of illustrative embodiments are described below with reference to the drawings. The illustrated embodiments are intended to illustrate, but not to limit, the disclosure. The drawings contain the following figures:

FIG. 5 is a side, cross-sectional view of a single layer implant, according to some embodiments.

FIGS. 6A-6C illustrate steps in a process for manufacturing an implant, according to some embodiments.

DETAILED DESCRIPTION

Figure 1:
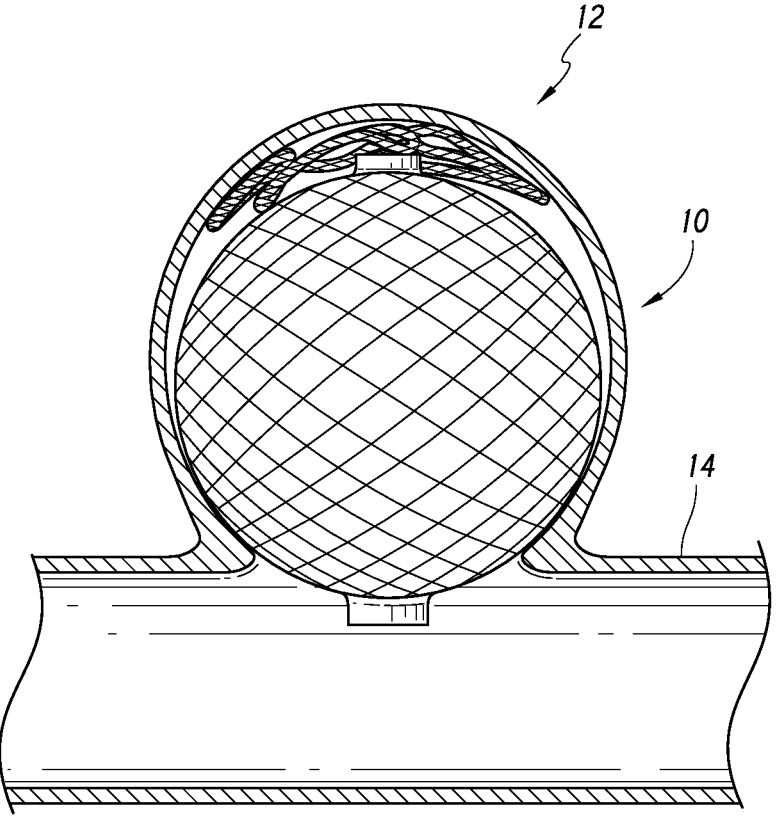
FIG. 1 is a cross-sectional side view of an implant expanded within an aneurysm, according to some embodiments.

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

Further, while the present description sets forth specific details of various embodiments, it will be appreciated that the description is illustrative only and should not be construed in any way as limiting. Additionally, it is contemplated that although particular embodiments may be disclosed or shown in the context of aneurysm therapy, such embodiments can be used in other applications for occluding vessels. Furthermore, various applications of such embodiments and modifications thereto, which may occur to those who are skilled in the art, are also encompassed by the general concepts described herein.

Delivery systems, implants, and methods of making the implants are provided herein. The implant can be useful for treating neurovascular defects. One use is in intracranial aneurysm embolization/occlusion and another in parent vessel occlusion (PVO) or sacrifice. Further, some embodiments can comprise features related to certain aspects of the present assignee's U.S. Pat. No. 8,142,456, the entirety of which is incorporated herein by reference.

In accordance with some embodiments disclosed herein, an embolization implant or device can comprise two or more sections having different shapes or configurations, which can enable the device to provide distinct functions or operational characteristics. The device can comprise a single, continuous piece of material that extends along each of the sections thereof. The piece of material can be shape set such that each of the sections achieves a desired shape or configuration. Accordingly, because some embodiments of the device use only a single piece of material, the device can advantageously integrate various functions previously performed by several devices into a continuous device. Thus, some embodiments allow the device to perform various discrete functions while operating as a unitary or single component.

For example, some embodiments of the implant can be formed from tubular braid stock comprising a resilient material such as Nitinol, that defines an open volume (ellipsoidal, spheroidal, spherical, substantially spherical/round, heart-shaped, ovoid, barrel-shaped or otherwise configured in cross section, etc.) in an uncompressed/unconstrained state. The device can be set within an aneurysm sac, such as at a vascular bifurcation. The implant can be delivered by access through the trunk vessel (e.g., the basilar artery), preferably through a commercially available microcatheter (not shown) with a delivery system, such as that described herein.

The device can comprise at least two portion: a first portion comprising an atraumatic tip, neck blocking, or framing portion, and a second portion comprising a volume-filling portion. In some embodiments, the first section can be configured to precede the second section when being placed into a body lumen that is to be occluded, such as an aneurysm. In such embodiments, a first portion or component of the device can be shape set to provide a function related to atraumatic entry into aneurysm or framing of an aneurysm. Further, a second portion, tip portion, or component of the device can be shape set to expand into one or more expandable components that can be advanced into an aneurysm to fill or pack the aneurysmal space or block the neck or ostium of the aneurysm to prevent herniation of embolic material therefrom. However, the order of placement can also be reversed, such as when the first section comprises a neck blocking portion.

In some embodiments, the first portion of the device can be shape set to a minimal cross-sectional dimension, profile, or diameter. For example, the first portion of the device can be drawn down, e.g., twisted or longitudinally straightened, to a minimum cross-sectional dimension and shape set such that when unconstrained, the first portion assumes the minimum cross-sectional dimension. Further, in some embodiments, the first portion can be shape set to provide a secondary configuration, such as a helical member or framing member. In some embodiments, the first portion can be shape set to comprise a flexible coil-type element or a series of interconnected expandable components. Thus, the first portion can, for example, serve an atraumatic protective, framing, or volume-filling function.

In some embodiments, the second portion of the device can be shape set to expand from a minimum cross-sectional dimension, when unconstrained, to an expanded profile that is much greater than the unconstrained profile of the first portion. For example, the second portion can expand to a round, three-dimensional shape, such as an ellipsoid, a cup, a barrel, and combinations thereof. Thus, the second portion can serve, for example, a volume-filling or neck blocking function.

Further, the second portion of the device can be shape set to a plurality of expandable interconnected components. For example, the second portion can expand into a series of interconnected ellipsoids. Various other shapes and features can be implemented, as discussed herein.

In some embodiments, the device can have a predetermined configuration, whether or not the device has only a single or multiple expandable components. The predetermined configuration can be based on typical aneurysm shapes, thereby allowing selection of a specific device. However, individual components of a device can also be arranged based on desired properties.

In some embodiments, expandable component(s) of the first or second portions of the device may be shape set or manufactured into a variety of geometrical or partial geometrical shapes.

For example, in order to accommodate a variety of aneurysm configurations, the shape or size of the expandable component(s) can be selected from a variety of spherical or non-spherical shapes, including, cylinders, hemispheres, noodles, polyhedrons (e.g., cuboids (types), tetrahedrons (e.g. pyramids), octahedrons, prisms), coils, prolate spheroids, oblate spheroids, plates (e.g., discs, polygonal plates), bowls (e.g., an open container, such as a hollow, hemispherical container or other open, hollow containers, whether hemispherical, rounded, or otherwise), non-spherical surfaces of revolution (e.g., toruses, cones, cylinders, or other shapes rotated about a center point or a coplanar axis), and combinations thereof.

A variety of delivery systems and procedures can be implemented to deliver a device having a specific size or shape and, in some embodiments, having a plurality of expandable components. Further, systems and methods are provided for delivery of a device to an aneurysm and/or recapturing the device for removal or repositioning. Examples of these systems and procedures are discussed further herein.

Additionally, although in some embodiments, a single device can be used alone to fill the aneurysm and provide a desired packing density or fill volume, a plurality of devices can also be used to fill the aneurysm and provide a desired packing density or fill volume.

Optionally, a liquid embolic and/or a framing component can be used in combination with one or more devices to facilitate delivery, engagement with the aneurysm, or increase of the packing density or fill volume. Any of these embodiments can allow increased packing density or fill volume to avoid recanalization of the aneurysm.

Referring now to the drawings, FIG. 1 illustrates an embodiment of an embolization device 10 positioned within an aneurysm 12 in a blood vessel 14. The device 10 can be particularly adapted for use in the tortuous neurovasculature of a subject for at least partial deployment in a cerebral aneurysm.

A cerebral aneurysm may present itself in the shape of a berry, i.e., a so-called berry or saccular aneurysm, which is a bulge in the neurovascular vessel. Berry aneurysms may be located at bifurcations or other branched vessels. Other types of aneurysms, including fusiform aneurysms, can also be treated using embodiments of the devices disclosed herein.

The device 10 can comprise at least one expandable component. In some embodiments, the device 10 can comprise a plurality of expandable components. Further, a given expandable component of the device 10 can have one or more different characteristics than another of the expandable components of the device 10. An expandable component can be formed from a material that can be highly compressed and later expanded when released into the aneurysm and contacted by a fluid, such as a fluid within the aneurysm.

Figure 2:
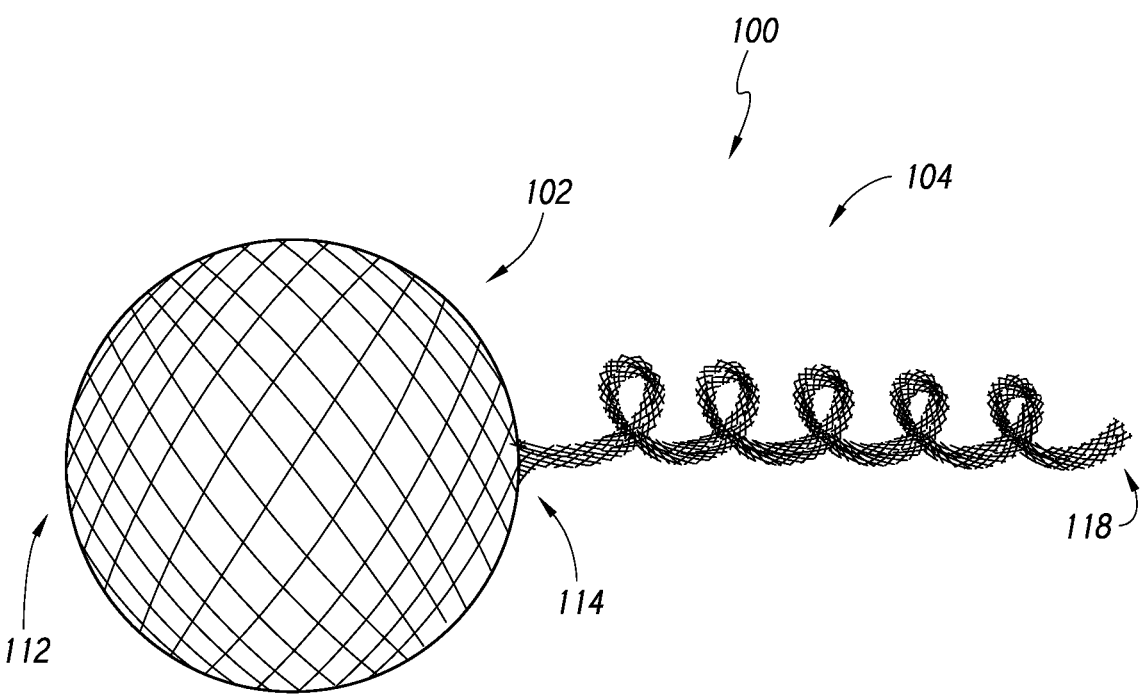
FIG. 2 is a side view of an implant, according to some embodiments.
Figure 3A:
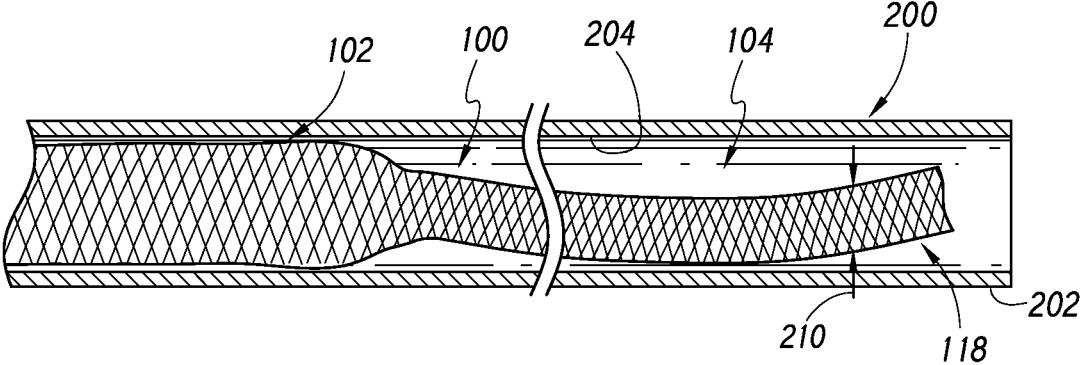
FIGS. 3A-3C are partial side, cross-sectional views of an implant in stages of deployment from a delivery catheter, according to some embodiments.
Figure 3B:
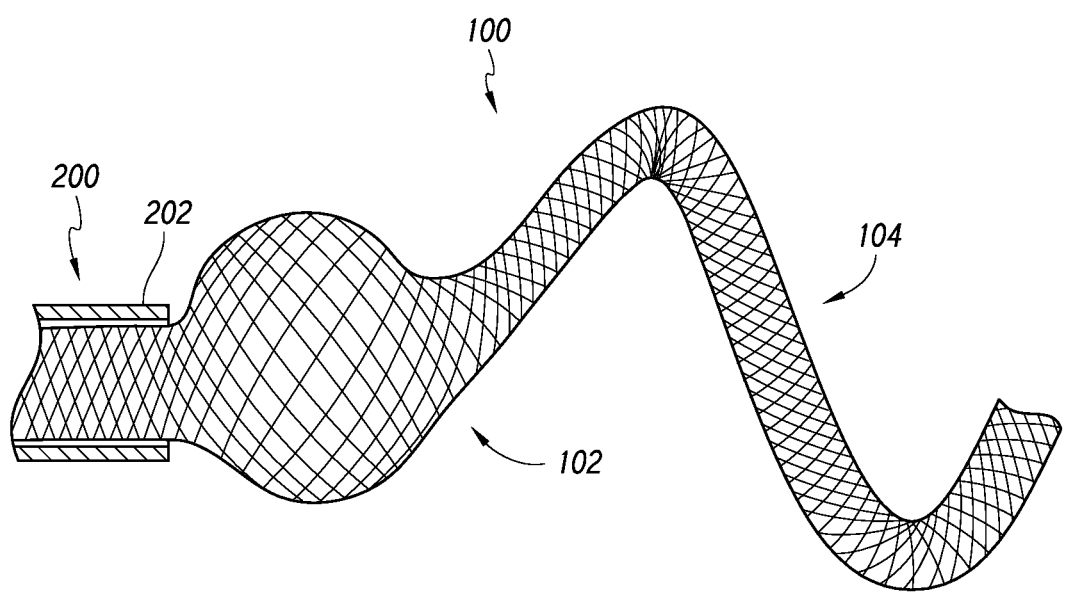
Figure 3C:
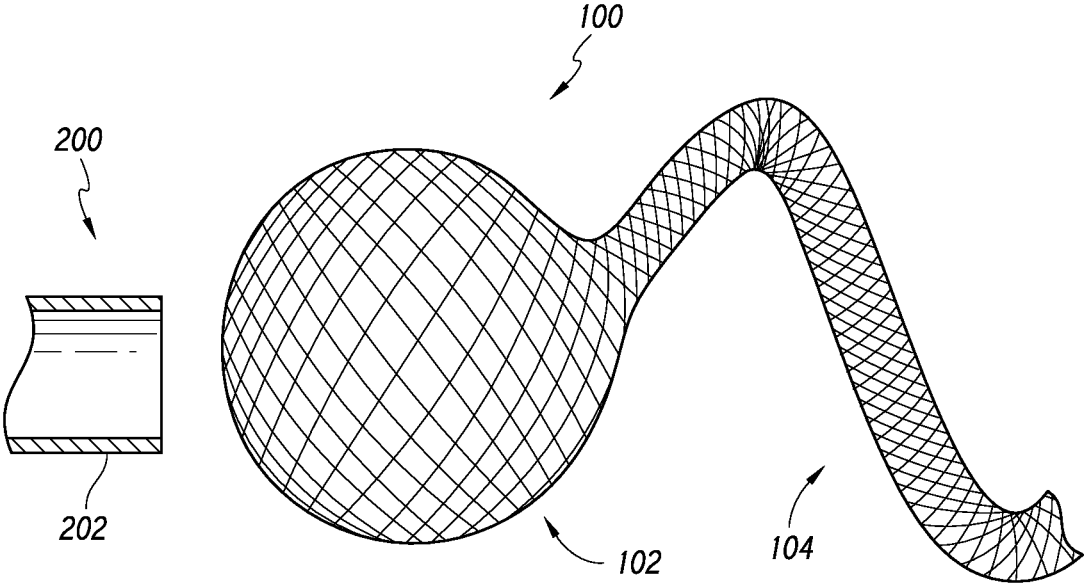

Referring now to FIGS. 2-3C, some embodiments can provide a device 100 having two or more expandable components. For example, the device 100 can comprise a first portion 102 and a second portion 104 that can each expand from a first or collapsed cross-sectional dimension or profile to an expanded cross-sectional dimension or profile. As discussed herein, the first portion 102 can comprise an expanded profile that is different in shape or size from the expanded profile of the second portion 104. As illustrated in FIG. 3C, the first portion 102 can comprise a generally globular shape while the second portion 104 can comprise a bundled configuration that extends in a helical path.

The device 100 can be formed from a continuous piece of material. For example, the material can comprise a plurality of braided filaments, a knitted material, or a woven material. Further, in some embodiments, the device 100 can comprise a tubular mesh that is shape set to define the first and second portions 102, 104. For example, with regard to the first portion 102, the tubular mesh can be shape set such that the first portion 102 defines an open volume and the filaments converge toward proximal and distal ends 112, 114 of the first portion to form a generally ellipsoidal shape.

In accordance with some embodiments, the first portion 102 can comprise any of a variety of three-dimensional shapes, such as ellipsoidal, spheroidal, spherical, substantially spherical/round, heart-shaped, ovoid, barrel-shaped, etc. In particular, in some embodiments, the first portion 102 can comprise a shape selected from the group consisting of cylinders, hemispheres, polyhedrons, prolate spheroids, oblate spheroids, plates, bowls, hollow structures, clover shapes, non-spherical surface of revolution, and combinations thereof. Additional expandable components can be provided that have substantially spherical shapes.

Additionally, the second portion 104 can comprise a shape different from that of the first portion 102. For example, the second portion 104 can comprise a helical shape, a zig-zag shape, a sinusoidal shape, or any of a variety of three-dimensional forms.

The device and tip portion are shown as being formed from the plurality of braided filaments. The second portion 104 can have a relatively large coil diameter (compared to the dimension of the first portion 102), which can create large coil loops. In some embodiments, a plurality of braided filaments can be bundled to form a coil having at least two and as many as ten loops. Further, in some embodiments, the second portion 104 can have between about three and about eight loops. Furthermore, in some embodiments, the second portion 104 can have about six loops.

Moreover, in some embodiments, the second portion 104 can extend along edges of a three-dimensional shape such that the second portion 104 operates as a framing member when inserted into an aneurysm.

Figure 11:
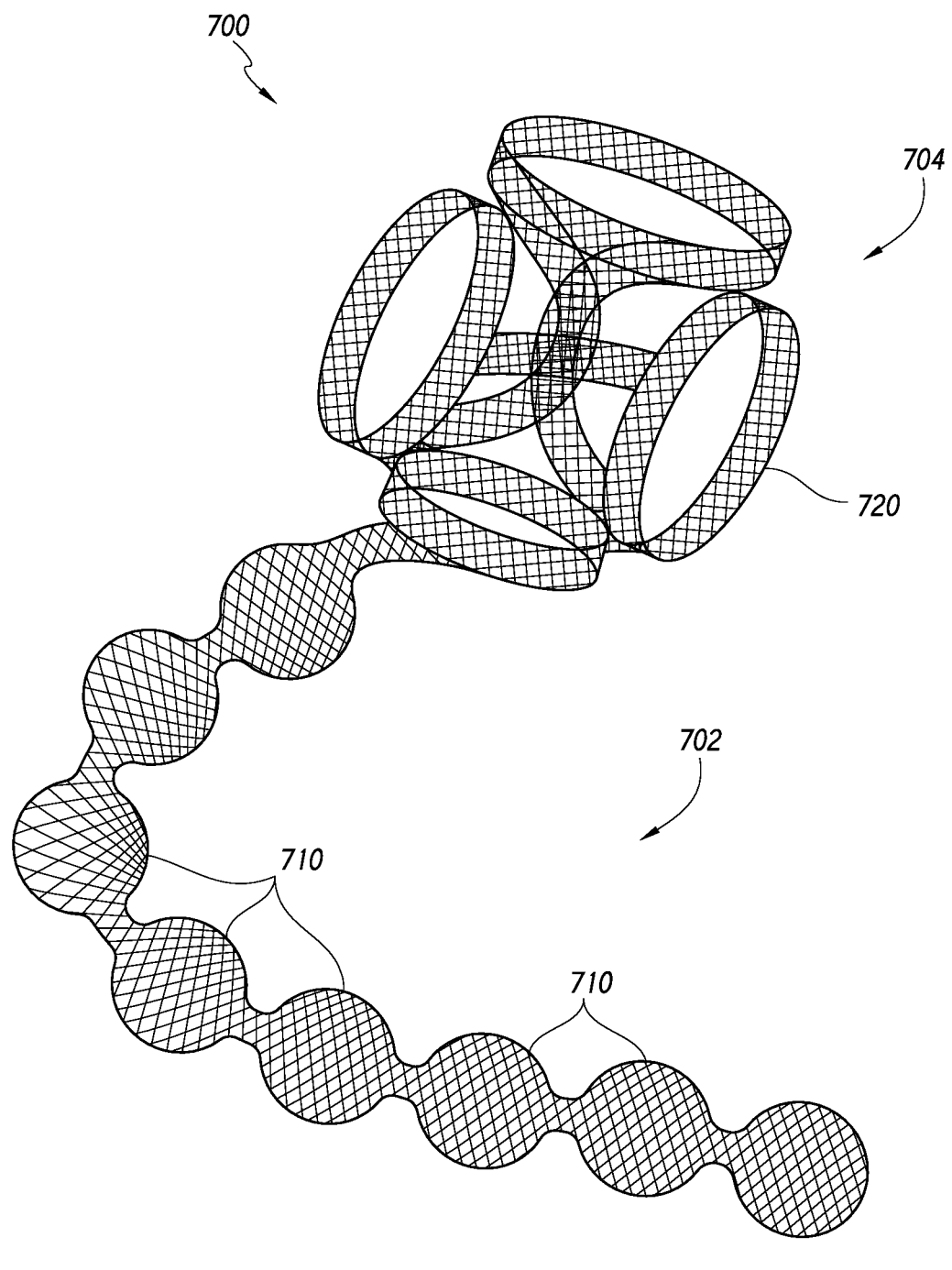
FIG. 11 is a perspective view of yet another configuration of an implant, according to some embodiments.

Optionally, the first and second portions 102, 104 can have different sizes. For example, the expanded profile of the first portion 102 can be greater than an expanded profile of the second portion 104, as illustrated in FIG. 2. However, as shown in FIG. 11, which illustrates that the second portion of the device can be formed into a framing member, the second portion of the device can comprise an expanded profile that is greater than the expanded profile of the first portion.

In accordance with some embodiments, the profile, size, or shape of the first and second portions 102, 104 can vary along their respective lengths. For example, in some embodiments, the first portion 102 can comprise a plurality of expandable components (see e.g., elements 710 of FIG. 11). In such embodiments, the plurality of components can expand to different profiles, sizes, or shapes. Similarly, the second portion 104 can also expand to a variable profile. For example, the second portion 104 can be shape set into a helical member that extends along a variable helical path. Further, the second portion 104 can comprise a helical member and a framing member, according to some embodiments.

In accordance with some embodiments, methods of placing an embolization device within an aneurysm are also provided. FIGS. 3A-3C illustrate a deployment sequence of a device 100 is moved through a catheter 200. These figures illustrate various stages of expansion or recapture of the device 100 within the catheter 200. In accordance with some embodiments of the methods disclosed herein, the device 100 can be partially released and recaptured into the catheter 200 after initial deployment into the fundus of the aneurysm. The placement of the device 100 can therefore be carefully selected in order to provide superior placement within the aneurysm and optimal results.

In some embodiments in which the delivery system enables a clinician to retrieve or recapture the device, the delivery/retrieval member can comprise the Alligator Retrieval Device, manufactured by Covidien LP. The Alligator Retrieval Device can include a flexible wire having a plurality of gripping arms or elements, e.g., four arms, at the distal end of the flexible wire. Other embodiments for the gripping elements include a clover leaf design, fish hook design, or dissolvable coupling.

Further, a suitable microcatheter adaptable for navigation through the tortuous neurovascular space to access the treatment site is disclosed in commonly assigned U.S. Pat. No. 7,507,229, the entire contents of which are hereby incorporated herein.

As shown in FIG. 3A, the device 100 can be advanced towards a distal end 202 of the catheter 200. In some embodiments, the device 100 can be pushed at the proximal end of the first section 102. However, the device 100 can also be pulled via attachment to a distal end of a guide wire or other member operative to advance the device 100 through the catheter 200 by applying a distal force at a distal end 118 of the second portion 104.

The catheter 200 can be selected such that an inner diameter of the lumen 204 closely approximates the first or collapsed, shape set cross-sectional dimension or profile 210 of the second portion 104. For example, in some embodiments, the second portion 104 can be shape set to a diameter of 0.021 inches. While being advanced through the catheter lumen 204, the second portion 104 can tend to avoid buckling if the catheter lumen 204 closely approximates the shape set diameter of the second portion 104. Accordingly, in some embodiments, the diameter of the lumen 204 should be less than two times the cross-sectional dimension or diameter of the smallest portion of the device 100. Preferably, the diameter of the lumen 204 is less than two times the cross-sectional dimension or diameter of the smallest portion of the device 100. Further, the diameter of the lumen 204 can be less than 1½ times the cross-sectional dimension or diameter of the smallest portion of the device 100.

Advantageously, the second portion 104 can provide a soft cushion or buffer for the device as the device 100 is placed into the aneurysm. Initially, the second portion 104 can be used to facilitate initial placement or location of the device 100 into the aneurysm. For example, the second portion 104 can be partially exposed (e.g., a sheath or catheter can be proximally retracted relative to the device 100 such that at least a portion of the second portion 104 extends from the distal opening of the sheath or catheter). The exposed portion of the second portion 104 can then be used to "anchor" or catch the assembly so that the device 100 and/or sheath/catheter can be further inserted into the aneurysm.

In some embodiments, the device 100 can comprise a radiopaque marker. For example, the radiopaque marker can be placed at the distal end 118 of the second portion 104. Accordingly, when advancing the device 100, the location and placement of the device 100 can be easily visualized under fluoroscopy. Further, in some embodiments, one or more filaments, materials, or coatings can be applied to either or both of the first and second portions 102, 104.

Once the device 100 and catheter 200 are properly positioned relative to the aneurysm (e.g., within the aneurysm or at least adjacent to the neck of the aneurysm so that the device 100 can be expanded into contact with the walls of the aneurysm), the device 100 can thereafter be expanded into contact with the walls of the aneurysm.

As shown in FIG. 3B, as the device 100 is advanced out of the distal end 202 of the catheter 200, the second portion 104 can expand. According to some embodiments, even when released from the catheter 200, the cross-sectional dimension of the second portion 104 will not tend to expand beyond a shape set cross-sectional dimension or diameter of 0.021 inches. Instead, the second portion 104 can expand to a secondary configuration, such as a helical member or framing member.

When released, as shown in FIG. 3C, the device 100 can expand from its first or collapsed configuration such that the first and second portions 102, 104 expand into contact with a wall of the aneurysm. In accordance with some embodiments, as the device 100 expands into contact with the walls of the aneurysm, the second portion 104 can provide a nest or volume of material against which the distal end, and in some embodiments, a marker or fastener at the distal end, can be placed. This can be especially advantageous to protect the aneurysm wall against any hub or noncompliant structure of the device (see e.g., element 322 of FIG. 4B).

For example, in some embodiments, the second portion 104 can comprise a bundle of the braided filaments, the second portion 104 can provide a substantial cushion or buffer into which the distal end of the device 100 can be safely nestled. Features of these and other embodiments can advantageously serve to gather the second portion 104 (e.g., the bundle of braided filaments, in some embodiments) into a bunch configuration that can be interposed between the distal end of the device 100 and the aneurysm dome in order to prevent or avoid puncture of the aneurysm dome, as illustrated in FIG. 1.

Figure 4A:
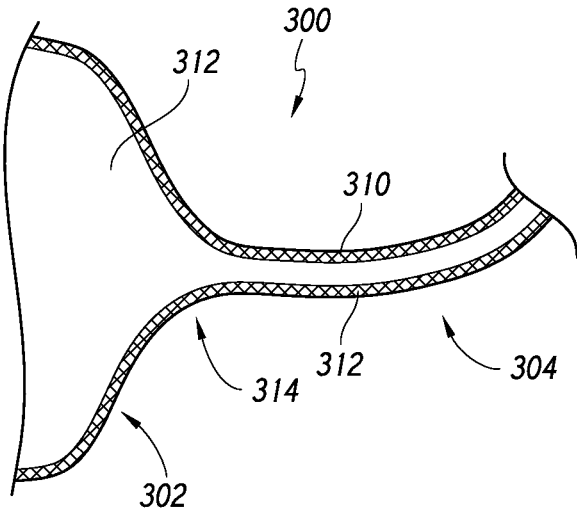
FIGS. 4A-4B are side, cross-sectional views of transition sections of implants, according to some embodiments.
Figure 4B:
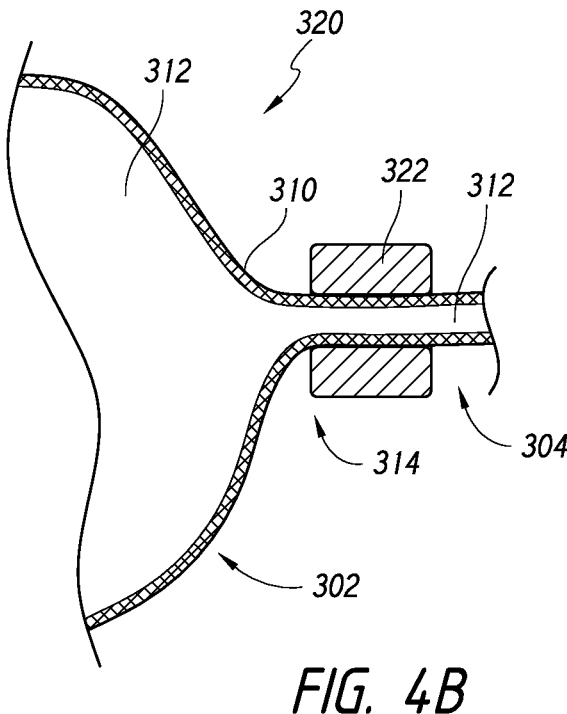

FIGS. 4A-4B illustrate side, cross-sectional views of devices 300, 320. With reference to FIG. 4A, the devices 300, 302 each comprise a first portion 302 and a second portion 304. As shown, the device 300 can comprise a single, continuous piece of material 310 that extends from the first portion 302 to the second portion 304. For example, the material 310 can comprise a tubular braid, knit, weave, or mesh. The tubular braid or mesh can comprise an inner lumen 312 that extends continuously from the first portion 302 to the second portion 304. However, as illustrated in both FIGS. 4A-4B, the inner profile or dimension of the lumen 312 can comprise a substantially zero cross-sectional dimension in the second portion 304. In accordance with any of the embodiments disclosed herein, the cross-sectional dimension can comprise a diameter or width.

For example, the cross-sectional dimension can be "substantially zero" even if the lumen 312 has open pockets. The term "substantially zero" can encompass configurations in which lumen 312 of the second portion 304 converges onto itself in a non-zero cross-sectional dimension, such as when the lumen 312 collapses with an inner surface thereof contacting itself in a shape set configuration. Furthermore, the term "substantially zero" can also refer to a contrasting (i.e., much smaller) size relative to the expanded dimension of the first portion 302. Indeed, when released from constraint, the cross-sectional dimension of the lumen 312 in the first portion 302 can expand to a degree much greater than the lumen 312 in the second portion 304.

Additionally, in accordance with some embodiments, the first and second portions 302, 304 can define a transition portion 314 whereat the material of the first portion 302 converges toward itself until achieving a substantially reduced profile whereat second portion 304 begins. In some embodiments, as shown in FIG. 4A, the transition portion 314 can be formed as a shape set configuration. However, in some embodiments, as shown in FIG. 4B, the transition portion 314 can further comprise a hub 322 that can secure the transition portion and urge the material 310 toward a reduced profile.

Figures 7, 8A, 8B, 8C:
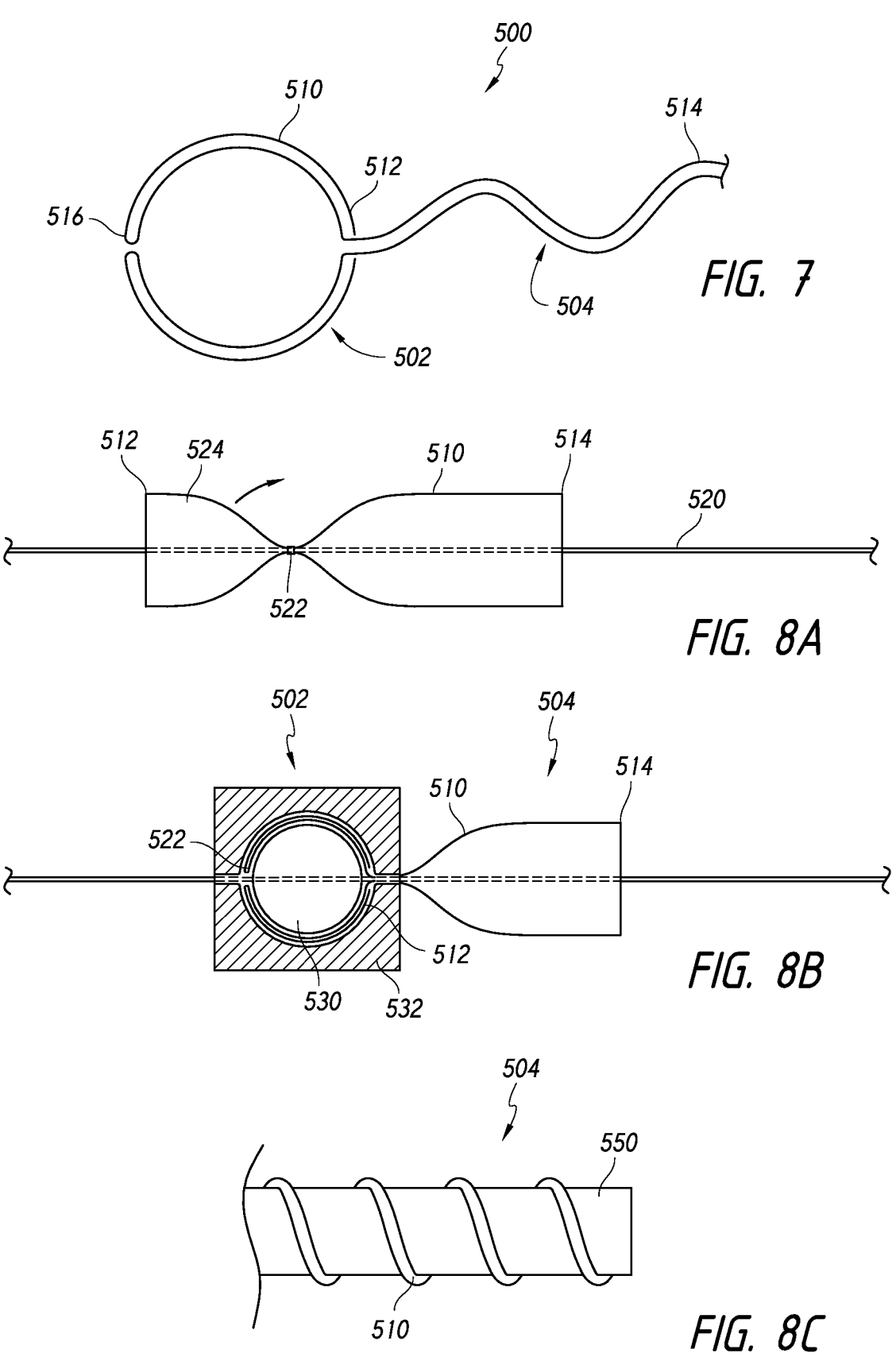
FIG. 7 is a side, cross-sectional view of a dual layer implant, according to some embodiments.
FIGS. 8A-8C illustrate steps in a process for manufacturing an implant, according to some embodiments.

Referring now to FIG. 5, another embodiment of an embolization device 400 is shown. The device 400 can comprise a single layer of material. For example, the device 400 can comprise a single layer of braided filaments. However, as illustrated in FIG. 7, at least a portion of an embolization device 500 can comprise multiple layers of material, such as braided filaments.

A process for manufacturing the device 400 of FIG. 5 is illustrated in FIGS. 6A-6C. As shown in FIG. 5, device 400 comprises a generally globular first portion 402 and a generally helical second portion 404. Initially, a single tubular braid 410 having a substantially constant inner dimension or profile is placed over a first wire 420, as shown in FIG. 6A. Thereafter, the braid 410 can be placed over a form 430. In some embodiments, once the form 430 has been inserted into the braid 410, a compression form 432 can be placed around the braid 410. The braid 410 can then be shape set such that the portion of the braid 410 fitted over the form 430 is shape set to a desired three-dimensional configuration.

Thereafter, a remaining portion 440 of the braid 410 can be longitudinally stretched, twisted, longitudinally straightened, or elongated along the longitudinal axis of the braid 410. This stretching of the braid 410 can draw down the cross-sectional dimension of the braid 410 in the remaining portion 440.

In accordance with some embodiments, the remaining portion 440 can also be physically modified. For example, one or more of the filaments of the remaining portion 440 can be cut and/or removed from the remaining portion 440. The alteration of the remaining portion 440 can facilitate the change of profile via shape setting and allow the second portion of the device to attain a desired configuration or profile.

When the remaining portion 440 is drawn down to a desired profile, the remaining portion 440 can be wound around a mandrel or wire 450 and shape set to a desired three-dimensional shape.

Additionally, as shown in FIG. 7, the device 500 can comprise a multilayer (shown in this embodiment as a dual layer) first portion 502 and a single layer second portion 504. The first portion 502 can be formed from a tubular braid that can be everted or inverted onto itself such that the braid extends continuously into layers. For example, as illustrated in FIG. 7, a tubular braid 510 can define a first end 512 and a second end 514. Additionally, the tubular braid 510 can define a folded end 516.

FIGS. 8A-8C illustrate an embodiment of a process by which the device 500 can be formed. As shown, the braid material 510 can be placed over a wire 520. A section 522 of the braid material 510 can be pinched or tied down onto the wire 520, for example, using a filament tie. The section 522 can then become the folded end 516 after a section 524 of the braid material 510 is everted over the section 522 and shape set in the step illustrated in FIG. 8B.

As shown in FIG. 8B, once the section 524 is everted, a form 530 can be inserted into the second end 514 of the braid material 510. A compression form 532 can then be positioned around the braid material 510 and the form 530 in order to shape set the first portion 502 of the device 500, similar to the discussion noted above with respect to FIG. 6B. Additionally, after the first portion 502 is shape set, the second portion 504 can be shape set by winding the braid material 510 around a mandrel 550 such that the second portion 504 is shape set to a desired configuration. Further details already discussed above with respect to FIGS. 6B-6C will not be repeated for brevity.

As such, in embodiments in which the device comprises an ellipsoidal shape, the ellipsoid can be enclosed within another ellipsoid to provide an ellipsoidal-shaped device having two layers. Thus, the first portion and/or the second portion of the device can comprise multiple layers. However, as shown in the embodiment of FIGS. 7-8C, although an additional layer can extend around the entire device or only around the second portion, some embodiments can advantageously be configured such that an additional layer extends only partially around the first or second portions of the device.

In accordance with some embodiments, the first portion of the device can comprise a volume-filling portion and/or a neck blocking portion, and the second portion of the device can comprise an atraumatic portion, volume filling portion, and/or a framing member. For example, FIGS. 1-4B illustrate embodiments of a device in which the first portion thereof comprises a volume-filling portion and the second portion comprises an atraumatic portion. FIGS. 9A-10B illustrate embodiments of a device in which the first portion thereof comprises a neck blocking structure and the second portion comprises a volume-filling and/or atraumatic portion. Further, FIG. 11 illustrates an embodiment of the device in which the first portion comprises a volume-filling portion and the second portion of the device comprises a framing member.

Figure 9A:
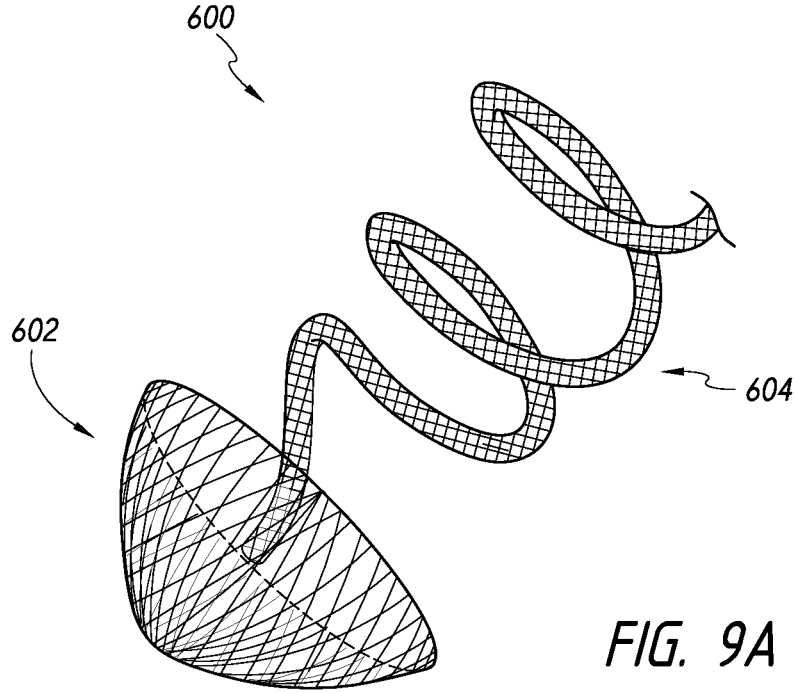
FIG. 9A is a perspective view of a configuration of an implant, according to some embodiments.
Figure 9B:
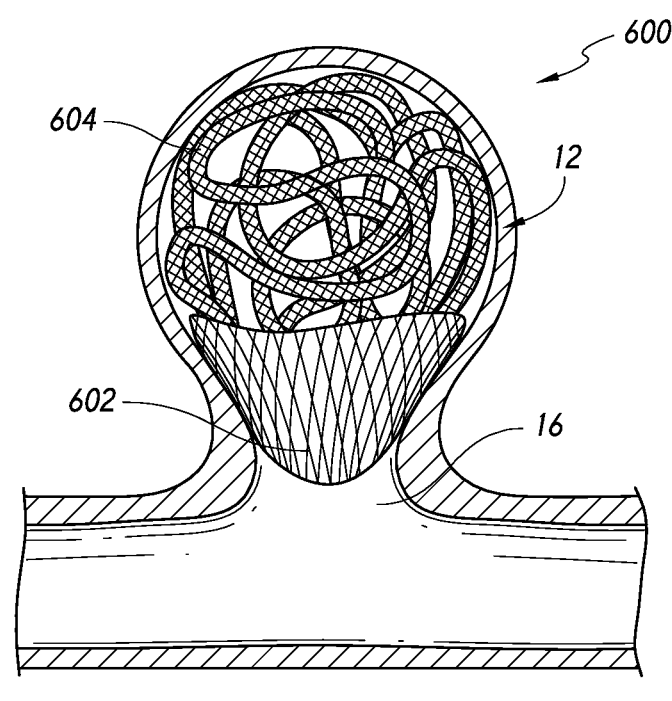
FIG. 9B is a side, cross-sectional view of the implant of FIG. 9A released into an aneurysm, according to some embodiments.

FIGS. 9A-9B illustrate a device 600 having a cup-shaped first portion 602 and a helically extending second portion 604. As discussed herein, the device 600 can be formed from a single, continuous piece of material such that the first and second portions 602, 604 are integrally connected with each other.

FIG. 9B illustrates placement of the device 600 into an aneurysm 12. As shown, the first portion 602 can be expanded into apposition with the vessel wall across the neck 16 of the aneurysm 12. Additionally, the first portion 602 can engage the vessel wall such that the first portion 602 is anchored across the aneurysm neck 16, thereby preventing herniation of the second portion 604 from within the aneurysm 12.

Figures 10A, 10B:
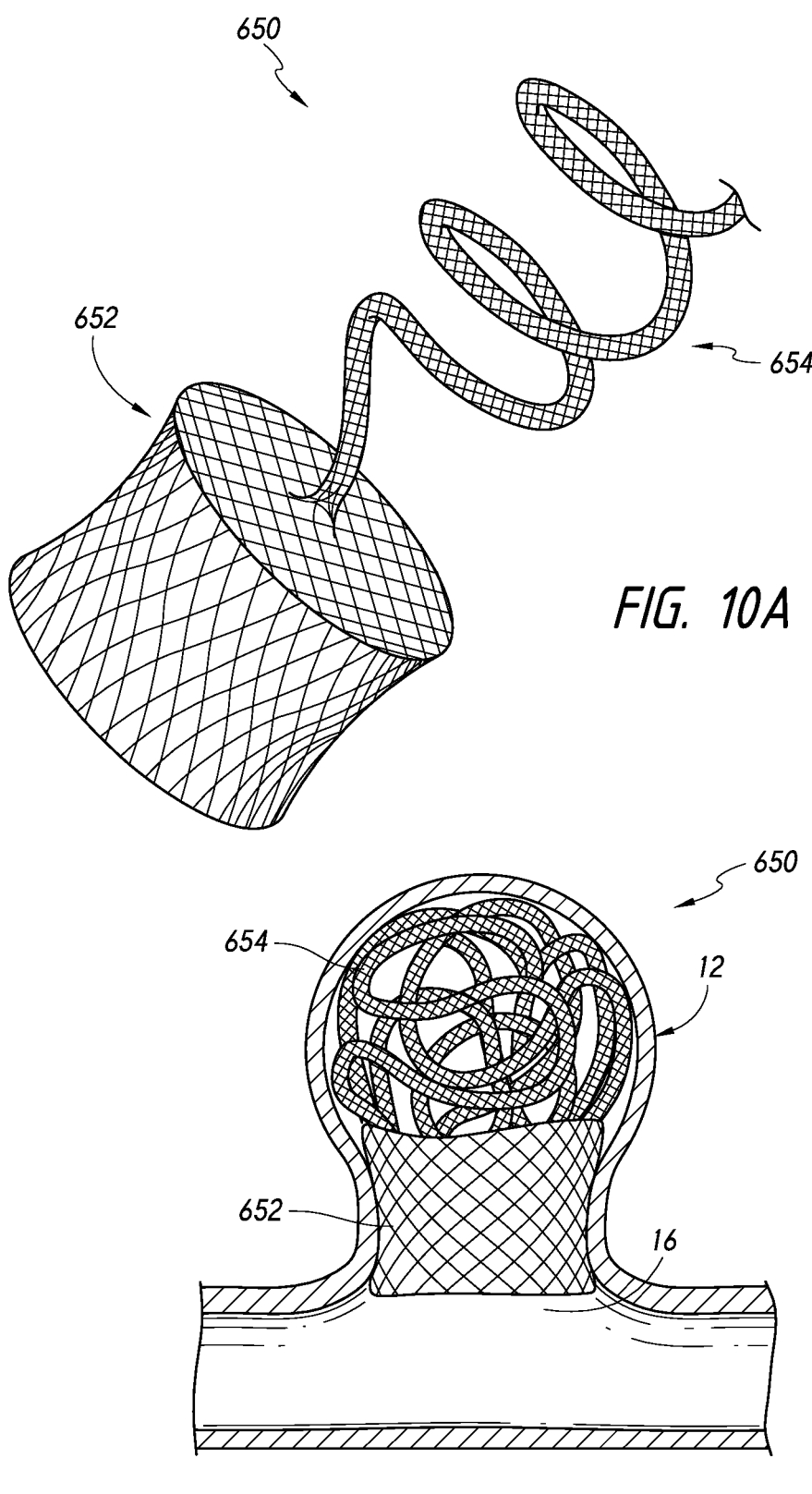
FIG. 10A is a perspective view of another configuration of an implant, according to some embodiments.
FIG. 10B is a side, cross-sectional view of the implant of FIG. 10A released into an aneurysm, according to some embodiments.

Similarly, FIGS. 10A-10B illustrate a device 650 having a cylindrically or barrel-shaped first portion 652 and a helically extending second portion 654. As also discussed herein, the device 650 can be formed from a single, continuous piece of material such that the first and second portions 652, 654 are integrally connected with each other.

FIG. 10B illustrates placement of the device 650 into an aneurysm 12. As shown, the first portion 652 can be expanded into apposition with the vessel wall across the neck 16 of the aneurysm 12. Advantageously, the first portion 652 can be configured to engage and press outwardly against the vessel wall at the neck 16, which can enable the device 650 to be useful in occluding wide neck aneurysms. The first portion 652 can engage the vessel wall such that the first portion 652 is anchored across the aneurysm neck 16, thereby preventing herniation of the second portion 654 from within the aneurysm 12.

FIG. 11 illustrates another embodiment of a device 700 comprising a first portion 702 and a second portion 704. The first portion 702 can comprise a plurality of individual expandable components 710. Any of the embodiments disclosed herein can comprise a plurality of components along the first portion. The device 700 advantageously utilizes a series of expandable components 710 because the second portion 704 is shape set as a framing member 720. As illustrated, the framing member 720 can comprise a plurality of loops or otherwise define a frame or structure having a hollow interior into which the expandable component 710 can be inserted during deployment of the device 700.

FIG. 11 also illustrates that the second portion of embodiments of the device can be shape set into a generally flat member. As shown, the framing member 720 comprises a series of loops formed by a flattened member.

In accordance with some embodiments, once the device 700 has been placed in the aneurysm, additional coils or embolic material can be advanced through an open end of the framing member 720. Suitable braid materials, structures, and method for manufacturing the framing member are disclosed in commonly assigned U.S. Pat. No. 6,168,622 to Mazzocchi, U.S. Pat. No. 8,142,456, issued Mar. 27, 2012, U.S. Patent Application Publication No. 2011/0319926, filed on Nov. 11, 2010, and U.S. Patent Application Publication No. 2012/0330341, filed on Jun. 22, 2011, the entireties of each of which are incorporated herein by reference. Braid materials may include stainless steel, nitinol cobalt chromium, or the like.

The framing member 720, combined with the expandable components 710 and optionally, coils or other materials, can provide the benefit of providing good neck coverage while preventing embolic devices from herniating into the parent artery. Additionally, the use of such a system can also increase packing volume efficiency and achieve stasis.

In placing the framing member 720 and the expandable components 710 within an aneurysm, the open end or widest interstices of the framing member 720 can be positioned at the neck of the aneurysm so as to facilitate insertion of the expandable components 710 and any additional material via a catheter, which can be placed into the open end or interstices of the framing member 720. In embodiments having a woven, knitted, braided, or mesh material for the framing structure, the braid pattern can be properly aligned to facilitate entry of the materials into the framing structure. As in other embodiments disclosed herein, the framing structure can comprise a radiopaque material or component that facilitates visualization and enables the clinician to align the framing structure as needed within the aneurysm.

The injection of a liquid embolic can increase the overall packing density or fill volume within the device.

One suitable liquid embolic is the Onyx™ liquid embolic system manufactured by Covidien LP, Irvine, Calif. Onyx™ liquid embolic system is a non-adhesive liquid used in the treatment of brain arteriovenous malformations. Onyx™ liquid embolic system is comprised of an EVOH (ethylene vinyl alcohol) copolymer dissolved in DMSO (dimethyl sulfoxide), and suspended micronized tantalum powder to provide contrast for visualization under fluoroscopy. Other liquid embolic solutions are also envisioned.

In accordance with some embodiments, at least a portion of the device can comprise a coating or material for enhancing therapeutic, expansive, or imaging properties or characteristics of at least one or every expandable component of the device.

In some embodiments, at least a portion of the device can be coated with a biocompatible material to promote endothelialization or provide a therapeutic effect.

The coating may include thrombogenic coatings such as fibrin, fibrinogen or the like, anti-thrombogenic coatings such as heparin (and derivatives thereof), or t-PA, and endothelial promoting coatings or facilitators such as, e.g., VEGF and RGD peptide, and/or combinations thereof. Drug eluting coatings and a drug eluting foam composite, such as anti-inflammatory or antibiotic, coatings are also envisioned. These drug eluting components may include nutrients, antibiotics, anti-inflammatory agents, antiplatelet agents, anesthetic agents such as lidocaine, and anti-proliferative agents, e.g. taxol derivatives such as paclitaxel. Hydrophilic, hygroscopic, and hydrophobic materials/agents are also envisioned.

In some embodiments, one or more portions of the device can also comprise an expansion-limiting coating that slows expansion of the component from its natural rate of expansion to a slower rate of expansion such that in the process of expanding, the position of the component can be adjusted within the aneurysm or the component can be removed from the aneurysm, if necessary. Examples of polymers that can be used as expansion-limiting coatings can include hydrophobic polymers, organic non-polar polymers, PTFE, polyethylene, polyphenylene sulfide, oils, and other similar materials.

In some embodiments, only specific segments of the device may be embedded or coated with an agent to provide desired characteristics to the expandable component(s). For example, the device can comprise a non-thrombogenic coating applied to less than the entire first portion or second portion to minimize clotting at this location. Such coatings may be desirable in aneurysms located at a bifurcation such that blood flow to branch arteries is permitted through the segment of the foam structure having the non-thrombogenic coating. The coated area may be a different color than the remaining portion of the expandable component to assist the surgeon in identifying this area.

Optionally, the coated area can also comprise radiopaque material to assist the surgeon in visualization and placement of portions of the device in a desired orientation relative to the aneurysm. The device can have radiopacity characteristics either by adding radiopaque filler to the piece of material, such as bismuth, or attaching radiopaque markers. Alternatively, a radiopaque material can be attached to the device, such as by dipping, spraying, or otherwise mechanically, chemically, or thermally attached, injected into, or blended into to the device.

According to some embodiments, if the device has a specific characteristic, such as a porosity profile, coating, shape, etc., intended for placement in a certain location of the aneurysm, the clinician can position the device by manually rotating, moving, maintaining the position of, or otherwise adjusting the position of the device within the aneurysm as the device expands. Thus, by gently manipulating the device, the clinician can adjust the device to ensure proper orientation of the device within the aneurysm. The position of the expandable device can be manipulated using various deployment or delivery devices.

Many of the features discussed herein can be used with any of the disclosed embodiments. For example, any of the embodiments can comprise an average porosity that varies spatially, any of the variety of disclosed shapes, any of the various disclosed materials or coatings, any of the disclosed 2-D or 3-D interconnected configurations, any of the disclosed inter-engagement configurations or structures, any of the disclosed delivery systems, etc.

The apparatus and methods discussed herein are not limited to the deployment and use of a medical device or stent within the vascular system but may include any number of further treatment applications. Other treatment sites may include areas or regions of the body including any hollow anatomical structures.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations may be made in the arrangement, operation and details of the method and apparatus of the subject technology disclosed herein without departing from the scope of the present disclosure. Unless otherwise expressed, reference to an element in the singular is not intended to mean "one and only one" unless explicitly stated, but rather is meant to mean "one or more." In addition, it is not necessary for a device or method to address every problem that is solvable (or possess every advantage that is achievable) by different embodiments of the disclosure in order to be encompassed within the scope of the disclosure. The use herein of "can" and derivatives thereof shall be understood in the sense of "possibly" or "optionally" as opposed to an affirmative capability.

We claim:

1. A method for occluding an aneurysm of a blood vessel, the method comprising:

advancing an intrasaccular device through a patient's vasculature to an aneurysm, wherein the intrasaccular device is advanced in a collapsed configuration within a lumen of a catheter, and wherein the intrasaccular device comprises an elongate member having a first longitudinal edge, a second longitudinal edge, and a broad surface extending between the first and second longitudinal edges, the elongate member comprising a plurality of braided filaments, wherein the elongate member includes a first portion for filling a volume of a cavity of the aneurysm and a second portion for framing the aneurysm, and wherein the second portion is positioned distal of the first portion when the intrasaccular device is in the collapsed configuration; and deploying the elongate member within the aneurysm cavity such that the elongate member assumes an expanded configuration in which the second portion forms a first loop wound about a first axis, a second loop wound about a second axis angled relative to the first axis, and a third loop wound about a third axis angled relative to at least one of the first axis or the second axis, wherein the first loop, the second loop, and the third loop define an interior region of the second portion and the first portion is positioned at least partially within the interior region, and wherein the broad surface of the elongate member along at least a portion of the first, second, and third loops of the second portion extends radially away from the interior region.

2. The method of claim 1, wherein at least two of the first loop, the second loop, or the third loop are non-overlapping.

3. The method of claim 2, wherein the first loop, the second loop, and the third loop are non-overlapping.

4. The method of claim 1, wherein, when the elongate member is in the expanded configuration, the second portion has an expanded cross-sectional dimension greater than that of the first portion.

5. The method of claim 1, wherein when the elongate member is in the expanded configuration, each of the first portion and the second portion forms a three-dimensional structure.

6. The method of claim 1, wherein the elongate member comprises a single, continuous piece of material.

7. The method of claim 1, wherein the elongate member comprises a flattened member.

8. The method of claim 1, wherein the resilient material comprises at least one of nitinol, stainless steel, or cobalt chromium.

9. The method of claim 1, wherein the elongate member comprises multiple layers of braided filaments.

10. A method for occluding an aneurysm of a blood vessel, the device comprising:

advancing an intrasaccular device through a patient's vasculature to an aneurysm, wherein the intrasaccular device is advanced in a collapsed configuration within a lumen of a catheter, and wherein the intrasaccular device comprises a primary structure formed of a flattened, tubular mesh having a first longitudinal edge, a second longitudinal edge, and a broad surface extending between the first and second longitudinal edges; and deploying the intrasaccular device within the aneurysm cavity such that the primary structure forms a secondary structure comprising a framing portion and a volume-filling portion, and wherein:

the framing portion comprises a first three-dimensional structure including a plurality of continuous loops defining an interior region of the framing portion therebetween, wherein at least two loops of the plurality of loops are angled relative to one another, the volume-filling portion comprises a second three-dimensional structure and is positioned within the interior region of the framing portion, and the broad surface of the mesh along at least a portion of the plurality of loops of the framing portion extends radially away from the interior region.

11. The method of claim 10, wherein a first loop of the plurality of loops is angled relative to a second loop of the plurality of loops, and wherein the first loop is adjacent to the second loop along a longitudinal dimension of the primary structure.

12. The method of claim 10, wherein the loops are non-overlapping.

13. The method of claim 10, wherein the volume-filling portion comprises a plurality of expandable components.

14. The method of claim 13, wherein at least one expandable component of the plurality of expandable components comprises a non-spherical surface of revolution.

15. The method of claim 10, wherein at least one of a profile, a shape, or a size of at least one of the framing portion or the volume-filling portion varies along a respective length of the at least one of the framing portion or the volume-filling portion.

* * * * *